(12) United States Patent
Chu et al.

(10) Patent No.: US 8,715,336 B2
(45) Date of Patent: May 6, 2014

(54) METHODS AND APPARATUS FOR TREATMENT OF ANEURYSMS ADJACENT TO BRANCH ARTERIES

(75) Inventors: Jack Chu, Santa Rosa, CA (US); David R. Erickson, Memphis, TN (US); Jonathon Morris, Santa Rosa, CA (US); Prema Ganesan, Oakland, CA (US); Curtis Hanson, San Marcos, CA (US); Matthew Rust, Santa Rosa, CA (US); Charles Thomas, Santa Rosa, CA (US); James Machek, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 899 days.

(21) Appl. No.: 11/737,432

(22) Filed: Apr. 19, 2007

(65) Prior Publication Data

US 2008/0262595 A1 Oct. 23, 2008

(51) Int. Cl.
*A61F 2/06* (2013.01)
(52) U.S. Cl.
USPC ........ 623/1.16; 623/1.31; 623/1.35; 623/1.13
(58) Field of Classification Search
None
See application file for complete search history.

(56) References Cited

U.S. PATENT DOCUMENTS

| | | | |
|---|---|---|---|
| 5,984,955 A | 11/1999 | Wisselink | |
| 6,152,937 A * | 11/2000 | Peterson et al. | 606/153 |
| 6,344,056 B1 | 2/2002 | Dehdashtian | |
| 6,428,565 B1 * | 8/2002 | Wisselink | 623/1.11 |
| 6,652,567 B1 | 11/2003 | Deaton | |
| 6,740,101 B2 | 5/2004 | Houser et al. | |
| 6,827,726 B2 | 12/2004 | Parodi | |
| 6,858,038 B2 | 2/2005 | Heuser | |
| 6,890,349 B2 * | 5/2005 | McGuckin et al. | 623/1.13 |
| 2002/0156517 A1 * | 10/2002 | Perouse | 623/1.11 |
| 2003/0093145 A1 | 5/2003 | Lawrence-Brown et al. | |
| 2004/0243215 A1 * | 12/2004 | Nelson | 623/1.12 |
| 2005/0038455 A1 | 2/2005 | Bates et al. | |
| 2005/0149166 A1 * | 7/2005 | Schaeffer et al. | 623/1.13 |
| 2006/0155359 A1 * | 7/2006 | Watson | 623/1.13 |
| 2007/0198053 A1 * | 8/2007 | Tatsumi et al. | 606/201 |

* cited by examiner

*Primary Examiner* — Thomas J Sweet
*Assistant Examiner* — Rebecca Preston

(57) ABSTRACT

A stent graft includes at least one aperture extending through the main body thereof, into which an extension portion may be deployed for positioning within an adjacent branch flow lumen. The extension portions include self biasing features, wherein the extension is biased into engagement with the main body to seal the interface thereof. Additionally, the extension portion may be configured for tortuous or deviated anatomy, to enable sealing of the extension portion with the body while extending the extension portion in a substantially non-radial direction from the main body.

8 Claims, 33 Drawing Sheets

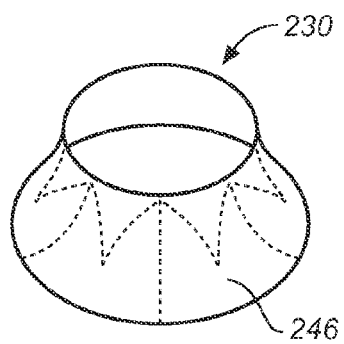
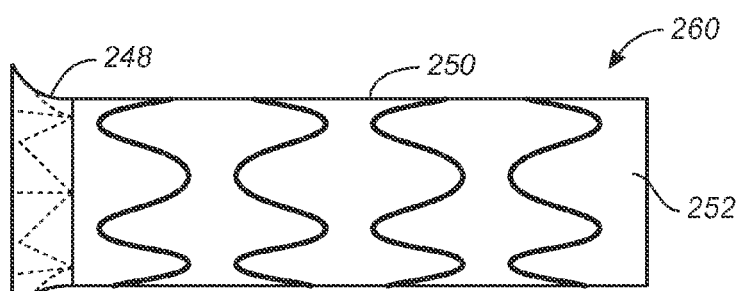
FIG. 36    FIG. 37
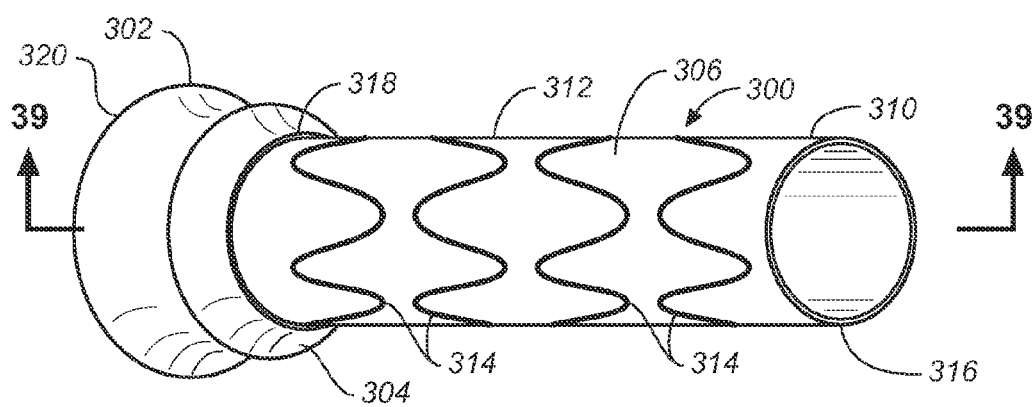
FIG. 38
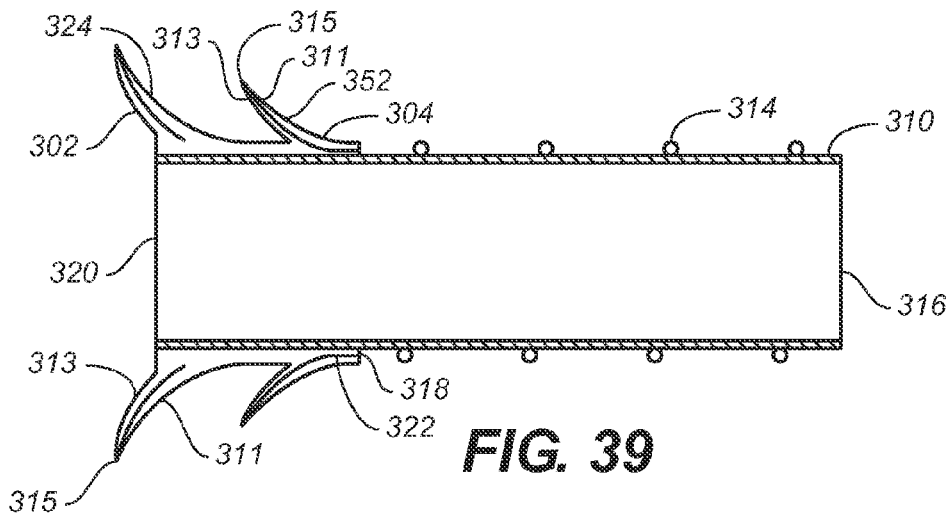
FIG. 39

METHODS AND APPARATUS FOR TREATMENT OF ANEURYSMS ADJACENT TO BRANCH ARTERIES

FIELD OF THE INVENTION

The field of the invention is the treatment of vascular abnormalities. More particularly, the field of the invention is the treatment of vascular abnormalities by placing an excluding device in a blood vessel to exclude or bypass an abnormality, including placing such an excluding device in an area near one or more branch vessels so as to bypass the abnormality, but not occlude the branch vessel.

BACKGROUND OF THE INVENTION

"Aortic aneurysm" is the term used to describe a vascular abnormality condition wherein a segment of the aorta is dilated to a diameter greater than its original diameter. Aneurysms can occur in virtually any region of the vasculature including the aorta in the abdominal and thoracic regions. Aortic aneurysms are caused by hardening of the arteries (atherosclerosis), high blood pressure (hypertension), genetic disposition such as Marfan's Syndrome, trauma or less common disorders. Atherosclerosis is the most common cause.

Where dilation of the aorta meets or exceeds 50% of the original aortic diameter, i.e., where the diameter of the aorta is 150% of the original or expected diameter, intervention generally is deemed necessary. Without intervention, the aneurysm may continue to expand, leading to the possibility of tearing or rupture of the aorta and death. Intervention includes techniques such as replacement of the aorta with a synthetic lumen which is sewn to the two ends of the still viable aorta after the aneurysmal portion has been opened or surgically removed, or, less invasively, by the endovascular placement of an exclusion device such as a stent graft across the aneurysmal site. The stent graft is a tubular member designed to provide a conduit within the aorta enabling blood flow through the aorta without allowing the systemic pressure of the blood to further stretch the aneurysm. For this intervention to be successful, the stent graft must span the weakened blood vessel wall so that the stent grafts' opposed ends engage and seal against healthy blood vessel tissue on the proximal and distal sides of the aneurysm.

A stent graft includes a stent (framework) portion which provides physical support of the stent graft in a tubular configuration once deployed at a vascular location, and a graft portion, comprising an excluding material, which is sewn or otherwise attached to the stent portion and which provides a relatively fluid-tight conduit for blood flow through the stent graft and past the aneurysm site. Placement of a stent graft can be performed without a chest incision, by using specialized catheters that are introduced through arteries usually at a location in a leg adjacent to the groin.

The aorta has numerous arterial branches. For example, the descending aorta includes the superior mesentery artery, the celiac trunk and the renal arteries. The proximity of an aneurysm to a branch artery may limit the use of an excluding device such as a tubular stent graft, as the main body or ends of the tubular stent graft may occlude or block the branch arteries due to the need for positioning of the stent graft at the location of healthy artery wall. Alternatively, there may be an inadequate length of healthy tissue for the stent graft to seal against in the area between the aneurysmal region of the artery and the location of the branch arteries. In this case, even if the stent graft initially is located without blocking a branch artery, there still is a risk of migration of the exclusion device to a position where it may partially or fully block a branch artery. Additionally, where multiple branch arteries are present adjacent to the aneurysm, the ability to position a stent graft so as not to occlude any of the branch arteries may be problematic. Furthermore, the aneurysm may implicate the aortic wall tissue adjacent to the branch arteries, for example the renal arteries, such that the aorta is dilated at the renal arteries, and the stent graft must extend over the renal arteries to have its ends seal against healthy aorta wall tissue.

To enable sealing off of the aneurysm from blood flow and simultaneously prevent occlusion of blood flow to the branch arteries, an artificial branch lumen may extend from the stent graft and into the branch vessel to a position wherein the distal end of the artificial branch lumen may contact and seal against healthy blood vessel tissue in the branch vessel. Thus, where an aneurysm extends adjacent to, or actually implicates, the branch vessel, a stent graft may still be deployed to exclude the aneurysm from further blood flow, by providing the artificial branch lumen to carry the blood flow into the branch lumen. However, the addition of an artificial branch lumen to the stent graft, and the deployment thereof, present additional complications for the physician attempting to successfully exclude the aneurysm. Where the artificial branch lumen is integrally provided with the stent graft, i.e., is affixed or attached to the stent graft main body at the time of deployment of the stent graft, the volume of the artificial branch lumen increases the cross section of the stent graft, thereby necessitating the use of a catheter of a larger crossing profile for deployment of the stent graft. In patient having restricted or diseased arterial anatomy, this increase in the diameter or crossing profile of the delivery catheter may preclude the ability to deploy the stent graft intravascularly, thus preventing treatment with a stent graft.

Alternatively, it may also be possible to first deploy a stent graft to span the aneurysmal location, and include in the stent graft one or more apertures which are then aligned, during deployment, with branch vessel locations which are spanned by the stent graft. Artificial branch lumens may then be located in these apertures, and extend therefrom and into the adjacent branch vessel to provide an artificial flow lumen for blood to flow from within the main body of the stent graft directly into the branch vessel. However, current schemes for providing a seal at the stent graft-artificial branch lumen interface can result unacceptable levels of leakage at the main body branch vessel interface, such that blood at systemic pressure can reach the aneurysm.

One circumstance which contributes to the occurrence of leakage is the situation where the branch vessel does not intersect with the aorta in a right angle or perpendicular relationship. As a result, the artificial branch lumen will need to extend at an acute angle from the sidewall of the stent graft, with a result that it may be difficult or impossible to effect a seal between the artificial branch lumen and the stent graft at the location where the artificial branch lumen extends from the aperture in the stent graft. An additional circumstance occurs where the artificial branch lumen is not properly extended from the stent graft when it is expanded into sealing engagement with the healthy wall tissue of the branch vessel, with the result that the artificial branch lumen may be located inside the lumen and away from the wall of the stent graft at the aperture in the stent graft and thereby fail to seal at the sealing interface of the artificial branch lumen with the stent graft. A sealing element attached to the artificial branch lumen is prevented from close engagement with the interior of the main body at the aperture.

SUMMARY OF THE INVENTION

Embodiments according to the present invention address aneurysm repair adjacent to and spanning branch vessel locations, wherein the stent graft assembly includes separately deployable artificial branch lumens which are sealingly engageable with a main stent graft body to provide reliable blood flow into the branch vessels.

Specifically, embodiments according to the present invention provide methods and apparatus for use in the treatment of aneurysms located near branch vessels with improved sealing paradigms for sealing the interface of a separately deployed extension and a main body of a stent graft and maintaining such sealing while also enabling placement of an excluding portion into the branch vessel even where the branch vessel opens in a non-perpendicular relationship between the general direction of the main flow lumen and with the general direction of the branch flow lumen. Thus, in one embodiment according to the invention there is provided an exclusion device useful for implantation in an aneurysmal site in a blood vessel having a branch vessel near the aneurysmal site comprising: a main body having at least one aperture therein alignable with an opening of a branch vessel from the blood vessel, and an artificial branch vessel which is configured to be deployed in sealing engagement with the aperture and to extend from the main body and into the opening of the branch vessel where the distal end thereof seals against the branch vessel wall. In one aspect, the artificial branch lumen includes, at the proximal end thereof, at least one expandable flange which, upon intravascular deployment thereof after deployment of the main body, is positioned against an interior surface of the main body adjacent to the aperture. In a further aspect, a first and a second expandable flange are provided adjacent the proximal end of the artificial branch lumen, such that upon deployment, one of the flanges is positionable against or upon the interior of the main body about the aperture, and the second of the flanges is positionable against or bears upon the exterior of the main body about the aperture. In a still further aspect, at least one of the flanges is self expanding when released from a delivery vehicle.

In an additional aspect, the artificial branch lumen includes a length compensation portion. In this aspect, the length or distance between the distal end of the artificial branch lumen, which is to be expanded into sealing engagement with healthy branch vessel tissue, and the proximal end of the artificial branch lumen, which is to be engaged with the main body of the exclusion device, may be varied. For example, after deployment of the main body portion, the artificial branch lumen is deployed through the aperture of the main body and into the branch vessel. Initially, the artificial flow lumen may be released from a guide sheath, and first expanded at its proximal end, to or engage the proximal end against the aperture and adjacent main body surfaces, then, the distal end portion of the artificial branch lumen is pushed away, such as by pushing on a wire or balloon tube which are captured within the distal portion of the artificial branch lumen, such that the proximal portion of the artificial branch lumen is pulled into the direction of the branch lumen opening, pushing any sealing arrangement thereof against the inner wall of the main body to help ensure maintenance of a seal at the aperture. The distal portion is then expanded, such as by inflating the balloon, to engage the distal portion against healthy branch vessel tissue. In one aspect, the artificial branch lumen is a woven element, wherein the frame and the sealing are accomplished by a woven tubular element of both structural and sealing materials.

In a yet another aspect, the artificial branch lumen is geometrically configurable, such that the artificial branch lumen is configured of at least two subsections, and the orientation of the subsections is variable, to enable the artificial branch lumen to extend from the main body and into an adjacent misaligned branch vessel, such as where the main body was misaligned upon deployment and the aperture therein is offset from the branch vessel location, or where the branch vessel extends at a severely acute (non-perpendicular) angle with respect to the surface of the main body.

BRIEF DESCRIPTION OF THE DRAWINGS

A more particular description of the embodiments may be had by reference to the embodiments according to the invention described in the present specification and illustrated in the appended drawings.

FIG. 36 is a perspective view of a renal extension flange employing the flange of FIG. 30;

FIG. 37 is a side view of a renal extension employing the flange of FIG. 36;

FIG. 38 is a perspective view of an alternative configuration of a renal extension, employing a double flange;

FIG. 39 is a sectional view of the renal extension of FIG. 38 at 39-39;

While the foregoing is directed to embodiments according to the present invention, other and further embodiments may be devised without departing from the basic scope thereof.

DETAILED DESCRIPTION

Reference now will be made to details of exemplary embodiments according to the invention. It is to be understood that the described embodiments are not intended to limit the invention solely and specifically to only these embodiments.

Methods and apparatus for stabilizing and treating an aneurysm include deploying an exclusion device, such as a stent graft, in the flow lumen of an aneurysmal blood vessel to span the aneurysmal location and seal off the aneurysmal location of the blood vessel from further blood flow while acting as a conduit to direct blood flow past the aneurysmal site. In the case of an abdominal aortic aneurysm near a branch artery, methods and apparatus for treatment include positioning an endovascular stent graft in the aneurysmal site, where the stent graft includes a body with one or more apertures therein (deployed in alignment with the opening of one or more branch vessels from the main vessel), and where branch inserts, deployed separately from the stent graft body, are extended through the apertures and into sealing engagement with the branch vessel walls, such that the deployment of the branch insert into the branch artery may act to maintain, or increase the likelihood of, effective sealing of the main body-branch insert interface.

The apertures of the main body of the stent graft are custom configured to be generally rotationally and longitudinally aligned with the opening of a branch vessel spanned (crossed) by the body of the stent graft, by manipulation of the rotational and longitudinal position of the body vis-à-vis the apertures during the intravascular deployment of the main body. Once the main body is deployed in the blood vessel, the artificial branch inserts are separately intravascular deployed to provide a sealed conduit extending from the apertures into the branch vessels.

Figure 1:
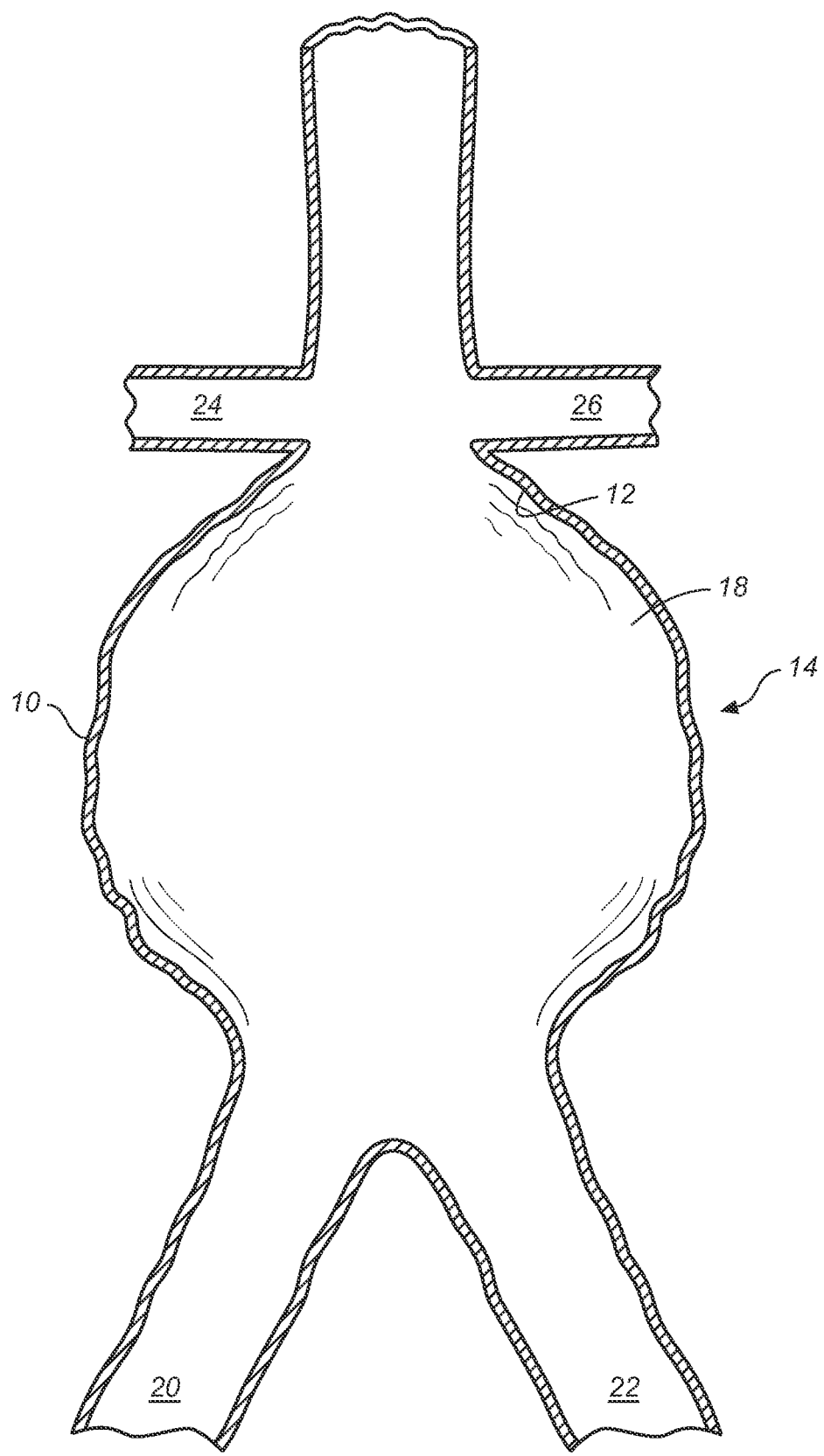
FIG. 1 shows a schematic cross section of an abdominal aorta having an aneurysm.

Referring initially to FIG. 1, there is shown an aneurysm of the abdominal aorta 10, such that the aorta 10 is enlarged at an aneurysmal location 14 at which the aorta wall 12 is distended and stretched. The distended and stretched aneurysmal location 14 forms an aneurysmal bulge or sac 18. If left untreated, the aorta wall 12 may continue to deteriorate, weaken, and eventually tear or burst. In the aorta 10 shown in FIG. 1, the aneurysmal sac 18 is located adjacent to, and upstream (blood flow direction) of, the bifurcation of the aorta 10 into the right iliac artery 20 and left iliac artery 22, and integral of (i.e., at least partially implicating), the opening of the renal arteries 24, 26 into the aorta 10 such that the aorta 10 is dilated at the renal artery 24, 26 location. Thus, to exclude the aneurysmal sac 18, the excluding device must span the renal arteries 24, 26, and, seal against the aorta wall 12 at a location upstream of the renal arteries 24, 26. While FIG. 1 shows renal arteries 24, 26 at 90 degrees to the aorta 10, the renal arteries 24, 26, may in anatomies be located not opposite one another and emanate up or down at angles other than 90 degrees.

Figure 2:
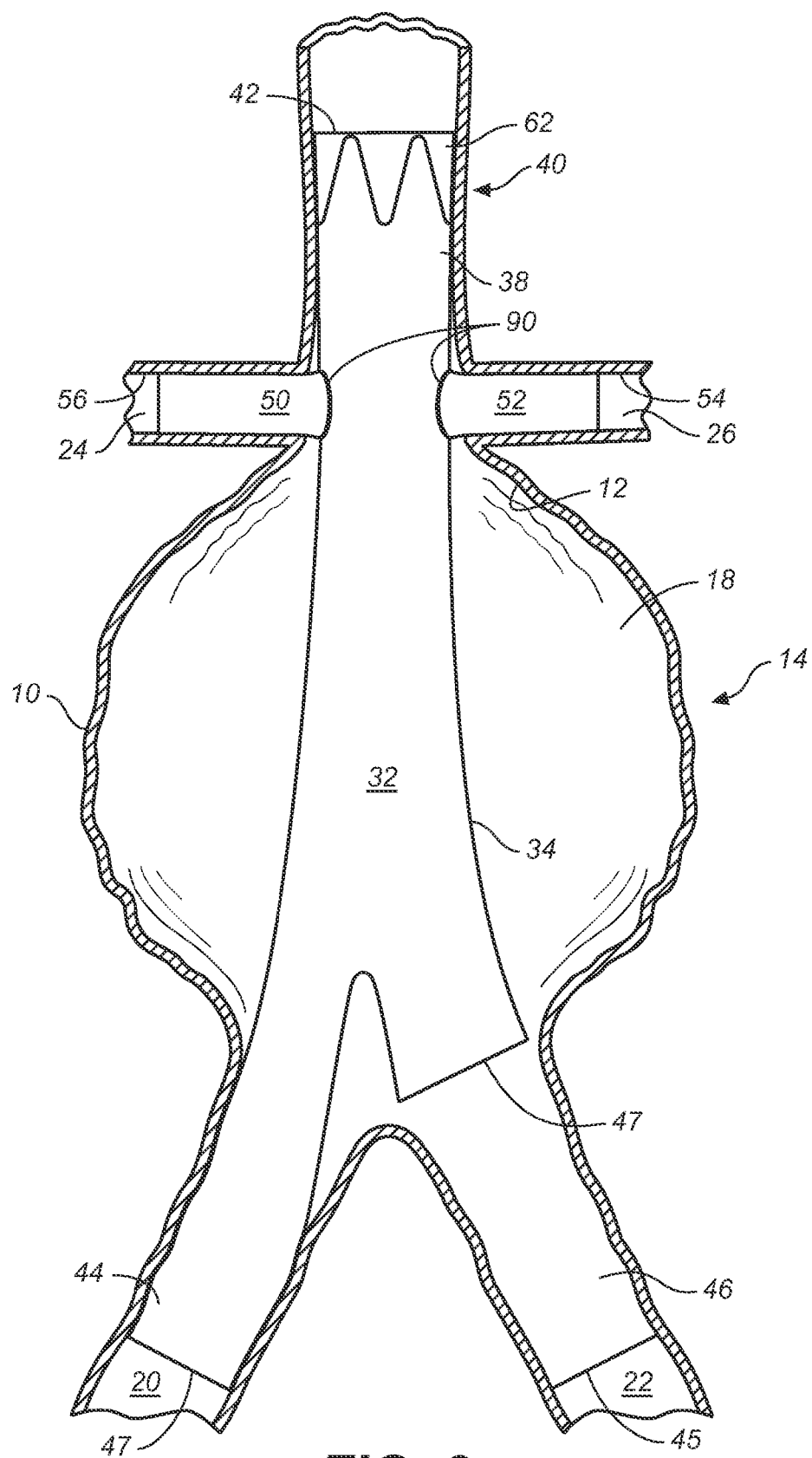
FIG. 2 shows a exclusion device (stent graft) deployed across the aneurysm seen in FIG. 1

Referring now to FIG. 2, a stent graft 32 is shown deployed in the aorta 10 to substantially exclude the aneurysmal sac 18 from blood flow at systemic pressure and sealingly engage against the aorta wall 12 at locations up and downstream of the aneurysmal sac 18. Stent graft 32 generally includes a main body 34 formed of graft material 38 and a stent framework 40 (of which only a single stent 62 may be seen in FIG. 2) as will be further described herein, and includes a first end 42 deployed upstream, from a blood flow perspective, from the renal arteries 24, 26, and at its opposite end, bifurcated right and left iliac legs 44, 46 terminating in open left and right ends 45, 47 respectively. Leg 44 may be integrally provided as an extension of the main body portion 34, and leg 46 may be a separate generally tubular member, which is separately deployed to the aneurysmal location and received in a leg aperture 47 provided in the main body 34 of the stent graft 32.

Stent graft 32, when deployed, sealingly engages against the inner walls of the iliac arteries 20, 22 by engagement of the stent graft 32 against the artery walls adjacent to the ends 45, 47 of the legs 44, 46 thereof, and extends therefrom to a position upstream, from the renal arteries 24, 26 to seal against the aorta wall 12. Thus, the stent graft 32 provides exclusion of the aneurysmal sac 18 from systemic blood flow by providing an artificial flow conduit through the aneurysmal portion of the aorta 10 through which blood, at systemic pressure, may freely flow. To enable blood flow from the aorta 10 into the renal arteries 24, 26, and simultaneously seal off the adjacent aneurysmal sac 18, the stent graft 32 also includes a pair of generally opposed (in the idealized case pictured here) renal extensions 50, 52, which extend through opposed apertures 90 in the body 34 and then across any gap between the stent graft 32 and the aorta wall 12 and into sealing engagement against the inner walls 54, 56 of the renal arteries 24, 26 while allowing fluid flow from the hollow interior of the main body 34 therethrough.

Figure 3:
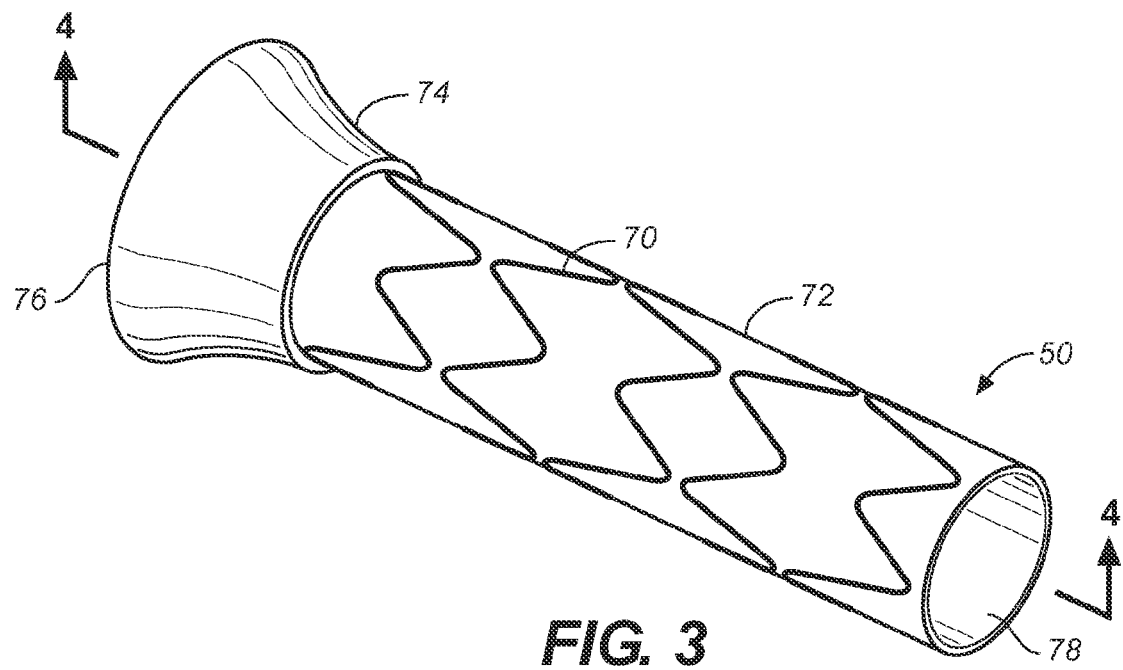
FIG. 3 is a partial perspective view of a renal extension of the exclusion device (stent graft) shown in FIG. 2.
Figure 4:
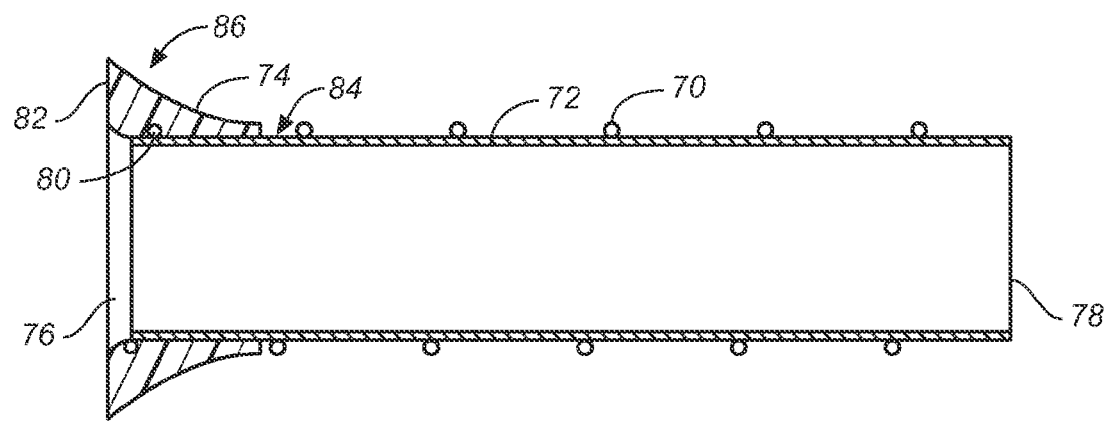
FIG. 4 is a sectional view of the renal extension of the exclusion device of FIG. 3.

Referring now to FIGS. 3 and 4, the structure and arrangement of inserts 50, 52, are shown prior to the placement thereof into a delivery sheath for intravascular deployment. In this embodiment, each of the inserts 50, 52 is of the same general construction, and for example insert 50 includes a stent framework 70, to which is sewn a tubular exclusion portion 72, and a conformable flange 74 formed about one end thereof. Insert 50 generally includes opposed open ends 76, 78, and maintains an open generally tubular profile after deployment between the main body 34 of the stent graft and the branch artery 54 by expansion of the stent framework 70. In this aspect of the insert 50, the stent framework 70 is configured of stainless steel or an other biocompatible material which is capable of being manipulated, in situ, to modify its configuration, such as from a compressed state to a tubularly expanded state, with a manipulation device such as a balloon. Exclusion portion 72 may be a plastic material, a woven Dacron, or other sheet like material which may be configured into a tubular shape, such as by being directly woven as a tube or as by a sheet of the material being folded over and sewn at its opposed edges to form a tube. Flange 74 may be configured of an elastomer, a plastic, or other biocompatible material which may be attached to the stent frame 70 and/or exclusion portion 72. As shown in the cross section of FIG. 4, the flange 74 is provided as a generally tapered structure, which includes a central, hollow generally right cylindrical interior 80 bounded at a first end 82 and an opposed second end 84, and a generally tapered outer circumferential face 86 tapering inwardly from first end 82 to second end 84. Upon deployment, circumferential face 86 engages against an aperture 90 (FIGS. 4 and 5) in the main body 34 of the stent graft to help provide sealing engagement therewith.

The flange 74 may be formed on insert 50 in a variety of ways. For example, the flange 74 may be formed by dipping the end 76 of the stent framework 70 and the exclusion portion 72 which were previously attached to one another such as by sewing or adhesively interconnecting the stent framework 70 and exclusion portion 72, in a liquid of the material to be used to form flange, and repeatedly removing, dipping, and removing the structure as coatings of the material are deposited thereon. Another mechanism involves placing the portion of the stent framework 70 and exclusion material combination 72 adjacent end 76 over a tubular mandrel, and covering the outer surface of the structure in a mold having a cavity generally conforming to the tapered outer circumferential face thereabout. A material, such as a plastic or an elastomer is then injected into the cavity, to form flange 74. Specific flange materials include silicone, polyurethane, polyurethane blends, polyurethane alloys, ePTFE, PET, polypropylene, polyethylene or other biocompatible materials. The flange 74 so constructed results in a physical structure which is compressible within the aperture 90 of a stent graft body 34, such that residual loading of the flange 74 against the aperture will occur after the extension 50, 52 is deployed, thus ensuring a greater likelihood of long term successful sealing of the aperture 90-extension 50, 52 interface.

Figure 5:
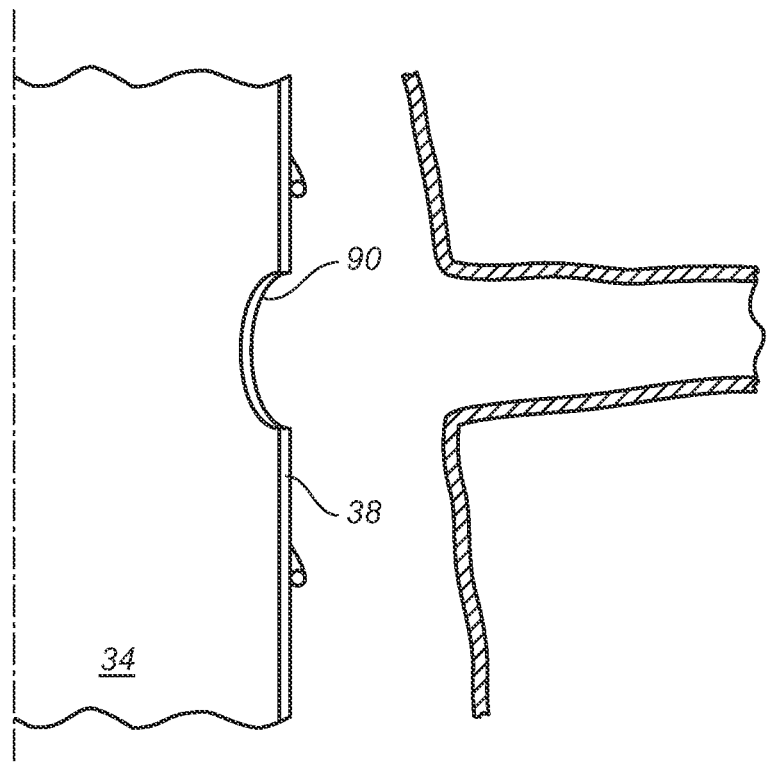
FIG. 5 is a partial, sectional view, of the exclusion device and abdominal aortic aneurysm of FIG. 2.
Figure 6:
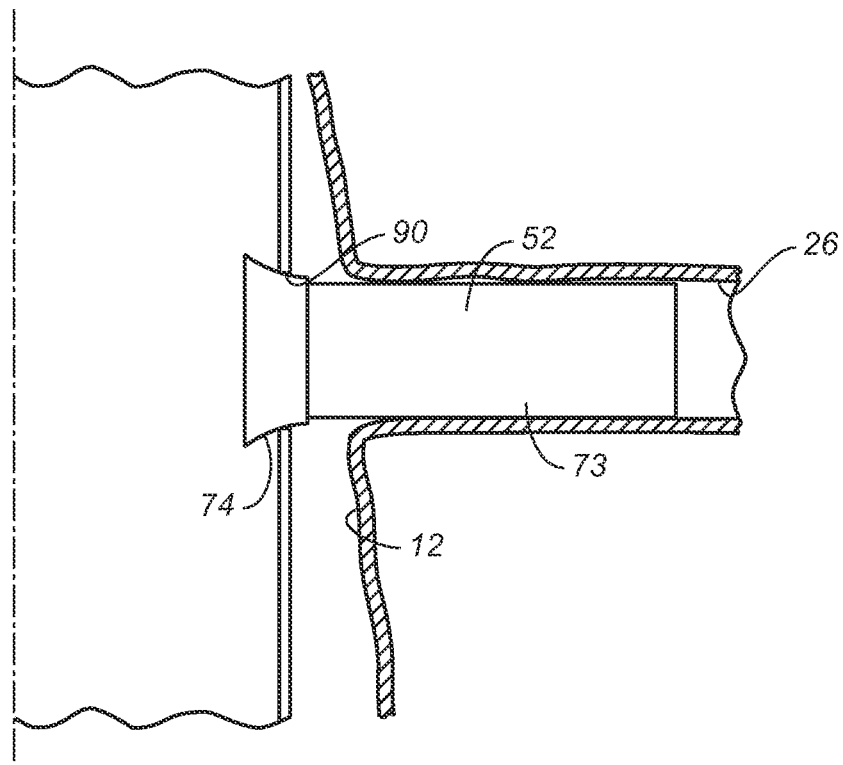
FIG. 6 is a sectional view of the portion of the exclusion device and abdominal aortic aneurysm of FIG. 5, having an arterial extension shown in plan view extending from a portion of the exclusion device into an adjacent renal artery.

Referring now to FIGS. 5 and 6, the location of the insert 52 (and likewise insert 50) with respect to the stent graft body 34 is shown. In FIG. 5, a portion of a main body 34 of the stent graft 32 deployed in a position spanning the renal artery 26 is shown as having an aperture 90 extending through the graft material 38 of the stent graft 32. Upon deployment of the insert 52 to the configuration as shown in FIG. 6, flange 74 of the insert 52 is located against the generally circular perimeter of the aperture 90 and also generally within the cylindrical body of the body 34, such that the generally tubular body 73 of the insert 52 formed of the stent framework 70 and exclusion portion 72 extends outwardly from the main body 34 and spans a gap between the body 34 and the adjacent aorta wall 12, and thence into the renal artery 26 where it sealingly engages against healthy renal artery wall 54 tissue inwardly from the opening of the renal artery 26 to the aorta 10. As will be further described herein, the position of end 78 of insert 50 vis a vis the opening of the renal artery 26 and the body 34 is selected, during deployment, to ensure that the flange 74 of the insert 50 will bear against the aperture 90 and the adjacent interior surface of the graft material 38 on body 34.

Referring now to FIGS. 7 to 27, the intravascular deployment of the stent graft shown and described with respect to FIGS. 1 to 6 is depicted. Initially, before deployment, each element constituting the stent graft 32 to be deployed must be prepared for delivery. In this discussion, each of the individual portions comprising the stent graft 32, including body 34, leg 36, and inserts 50, 52 are configured with stainless steel or other biocompatible structural material to form their individual stent frameworks, and thus in one configuration a balloon is needed to expand each of these elements in situ. However, it is specifically contemplated herein that the body 34 and leg 36 may be configured to include a shape memory stent framework, such that the body 34 and leg 36 are self expanding when released from a delivery device.

Figure 7:
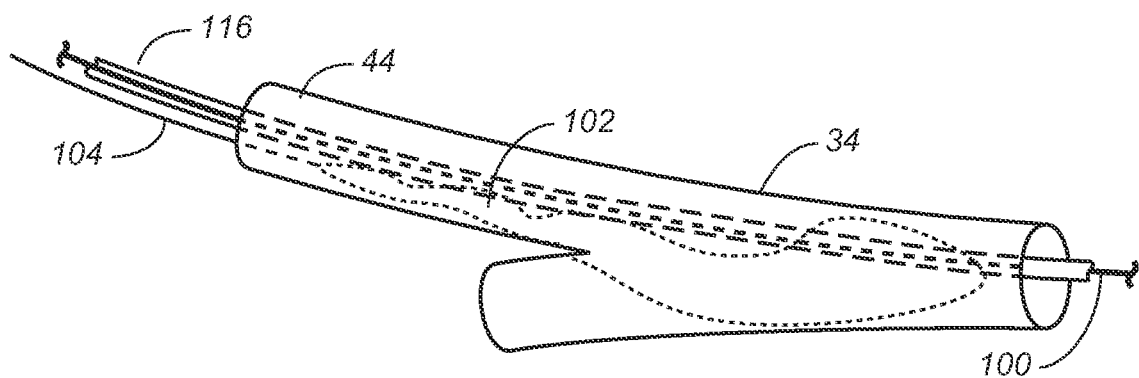
FIG. 7 is a perspective view of a portion of the exclusion device of FIG. 2 being prepared for deployment in an abdominal aortic aneurysm.
Figure 8:
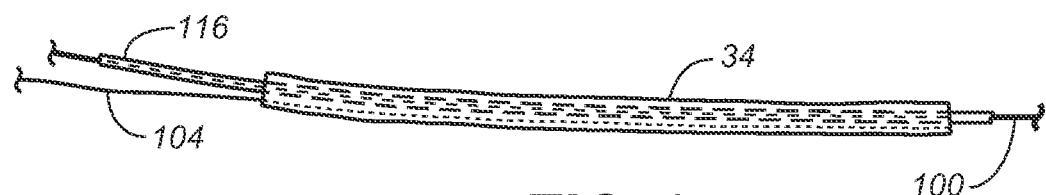
FIG. 8 is a perspective view of the portion of the exclusion device of FIG. 7, showing the portion of the exclusion device compressed for placement in a delivery device for deployment in an abdominal aortic aneurysm.
Figure 9:
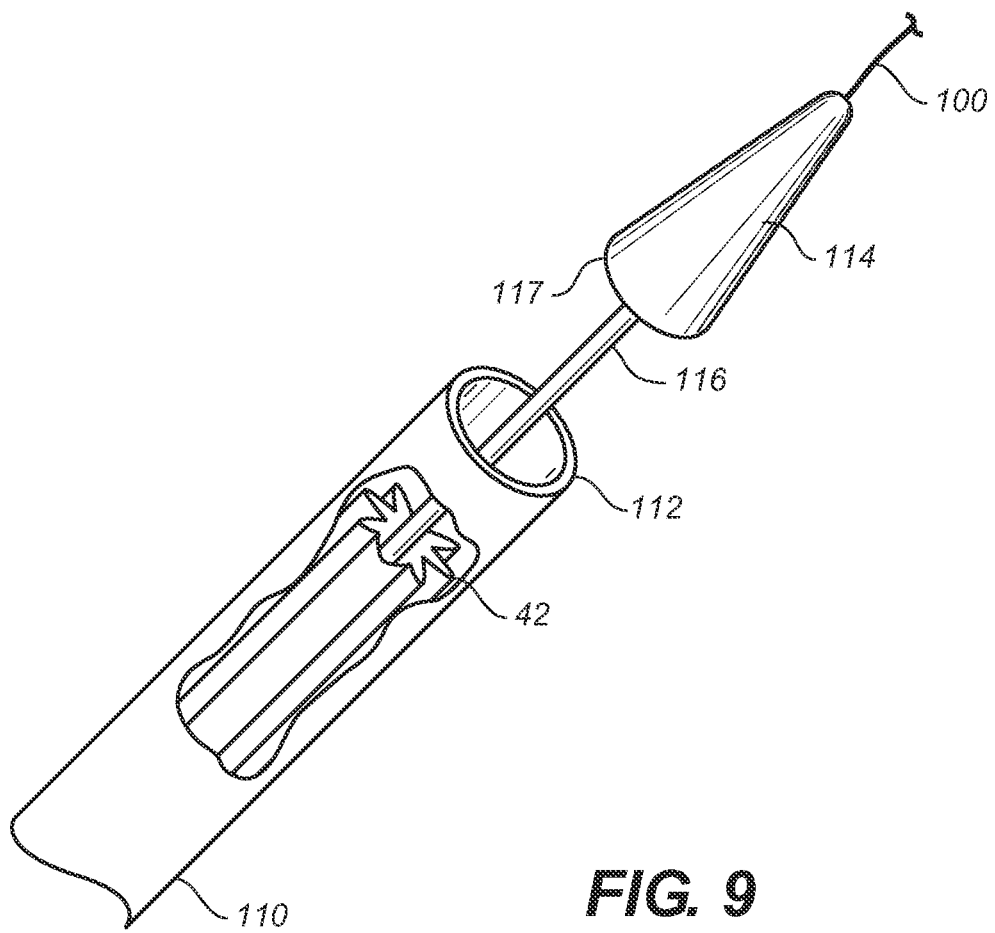
FIG. 9 is a partial perspective view of a delivery device, shown partially in a cut-away view, for deploying the portion of the exclusion device of FIG. 8 into an abdominal aortic aneurysm.

Referring initially to FIG. 7, a body 34 of a stent graft to be deployed is shown, and has a guidewire 100 extended through the tubular interior thereof and outwardly of leg 44, a balloon 102 loaded within the hollow interior, having inflation lumen 104 connected thereto and a tapered central catheter 116 extended therethrough and exiting leg 44. Additionally, radiological markers are provided adjacent to the opposed ends of the main body 34, at each opening of the main body 34. After the wire 100, catheter 116 and balloon 102 are positioned as shown, the body 34 is compressed (FIG. 8) such that it will fit within the tubular interior of a delivery sheath 110. As shown in FIG. 9, the compressed body 34 is received within delivery sheath 110 (shown partially in cutaway), such that the end 42 thereof is disposed inwardly of, but adjacent to, the deployed end 112 of the delivery sheath 110. Additionally, a tapered tip 114 is provided, with a central aperture therethrough through which the guidewire 100 extends, such that the base 117 of the tapered tip 114 may be releasably seated against the open deployment end 112 of the delivery sheath 110, by manipulating the central catheter 116 which is attached to the tapered tip 114. Thus, the tapered tip 114 may be used to help guide the sheath 110 through tortuous anatomy and protect the main body 34 therein, while not interfering with the deployment of the main body 34 when the sheath is retracted. The procedure of extending wires and catheters through the tubular portions of the stent graft, and the placement of balloon(s) therein, is repeated for each of the remaining elements, such that each of the insert 50, insert 52, and the leg 46 are located adjacent to, and spaced from, an open end of a respective delivery sheath 110', 110" and 110''', with balloons, guidewires, central catheter members, and tapered tips likewise in place.

Figure 10:
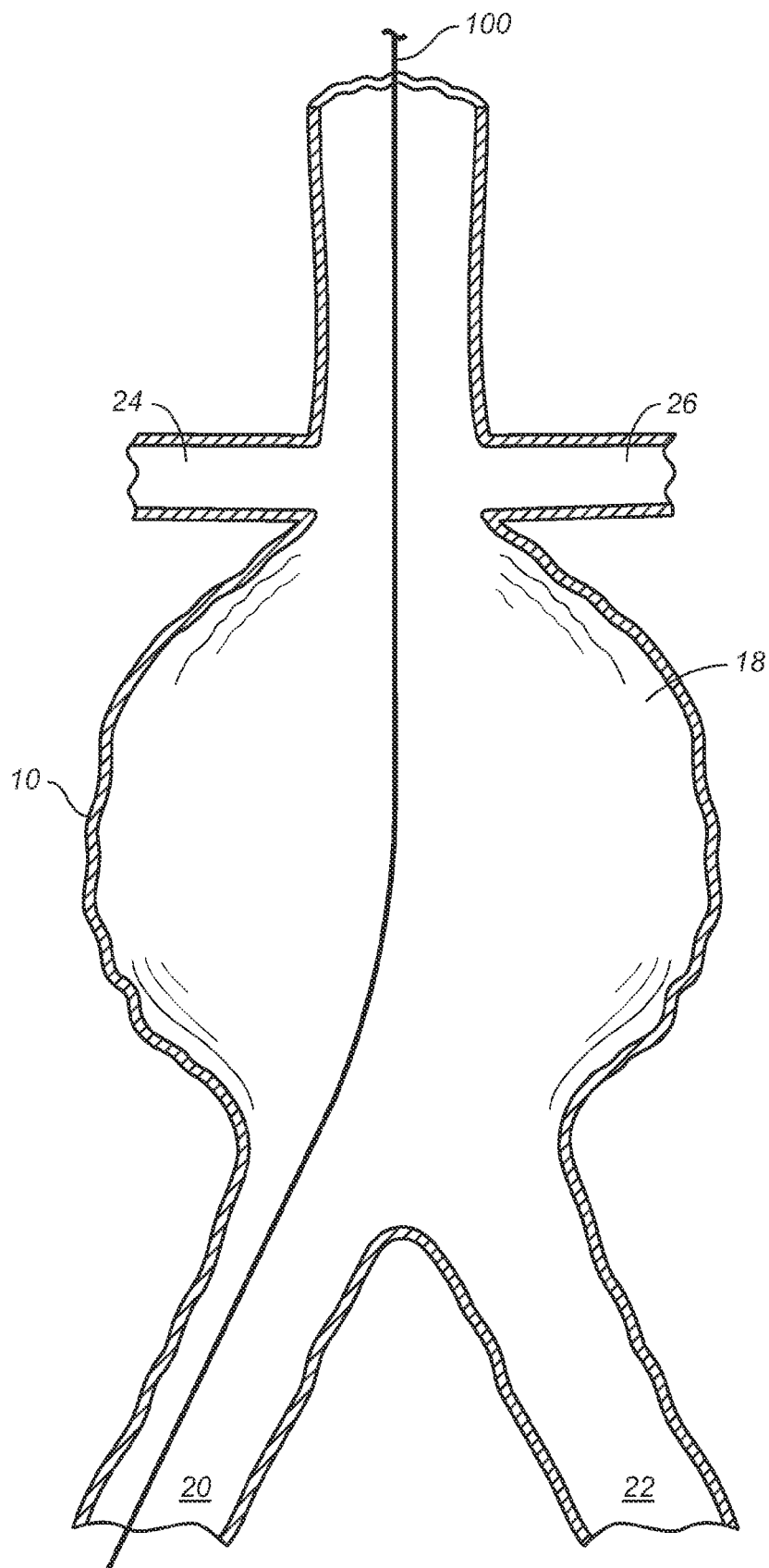
FIG. 10 is schematic view of the abdominal aneurysmal aorta of FIG. 1, showing a guidewire extending through the aorta.
Figure 11:
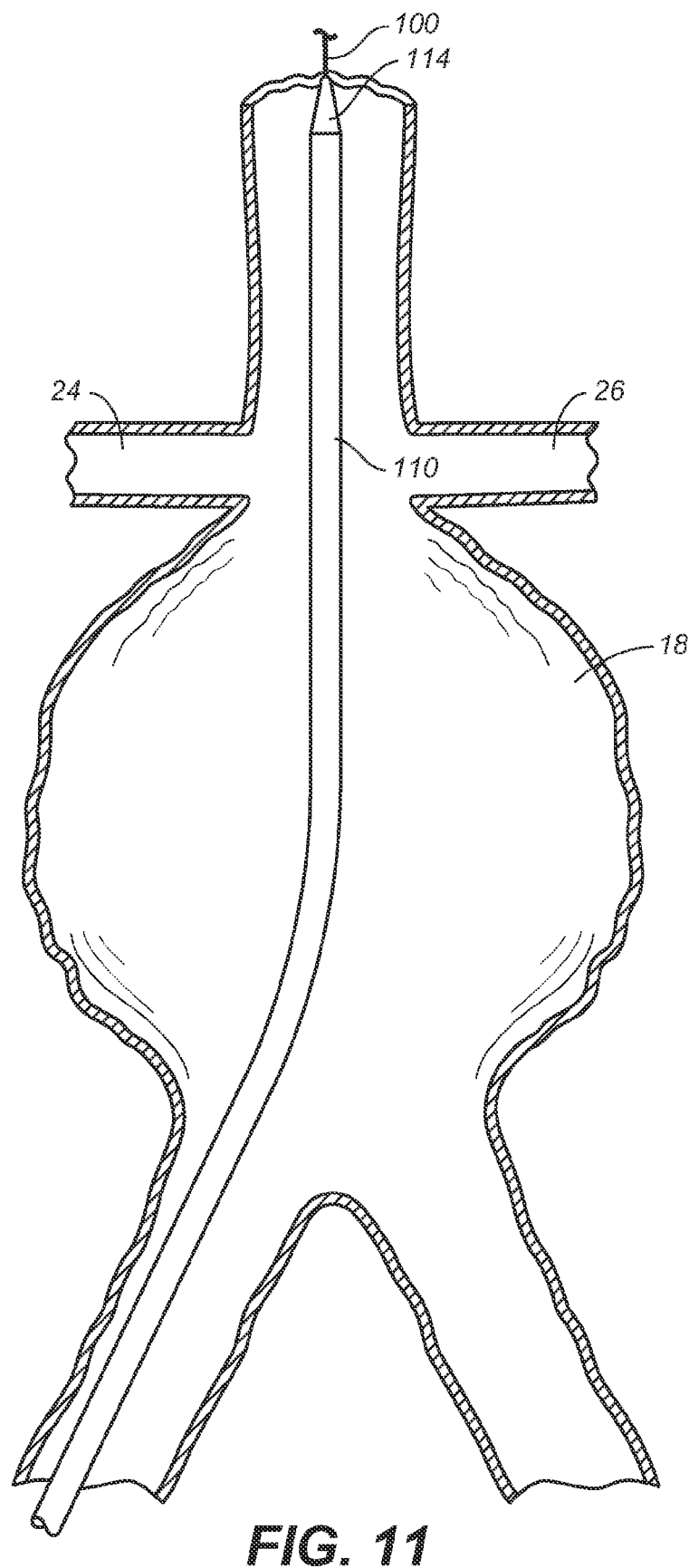
FIG. 11 is a schematic view of the abdominal aneurysmal aorta of FIG. 1, showing a delivery device for deploying the portion of the exclusion device of FIG. 7 extending through the aneurysmal portion of the aorta and positioned to begin deployment of the portion of the exclusion device of FIG. 7.
Figure 12:
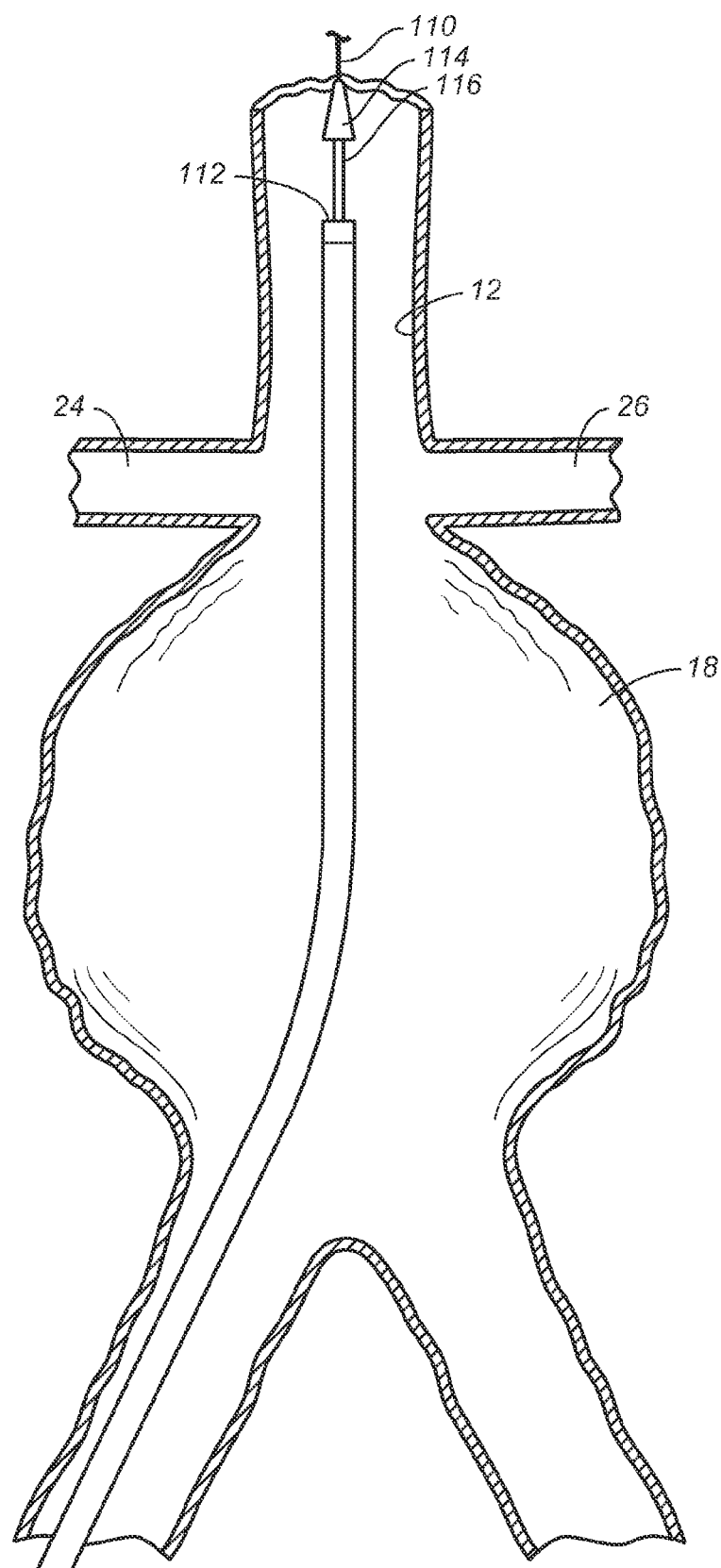
FIG. 12 is a schematic view of the abdominal aneurysmal aorta, having the delivery device ready for deploying the portion of the exclusion device of FIG. 7 to span the aneurysmal portion of the aorta therein.
Figure 13:
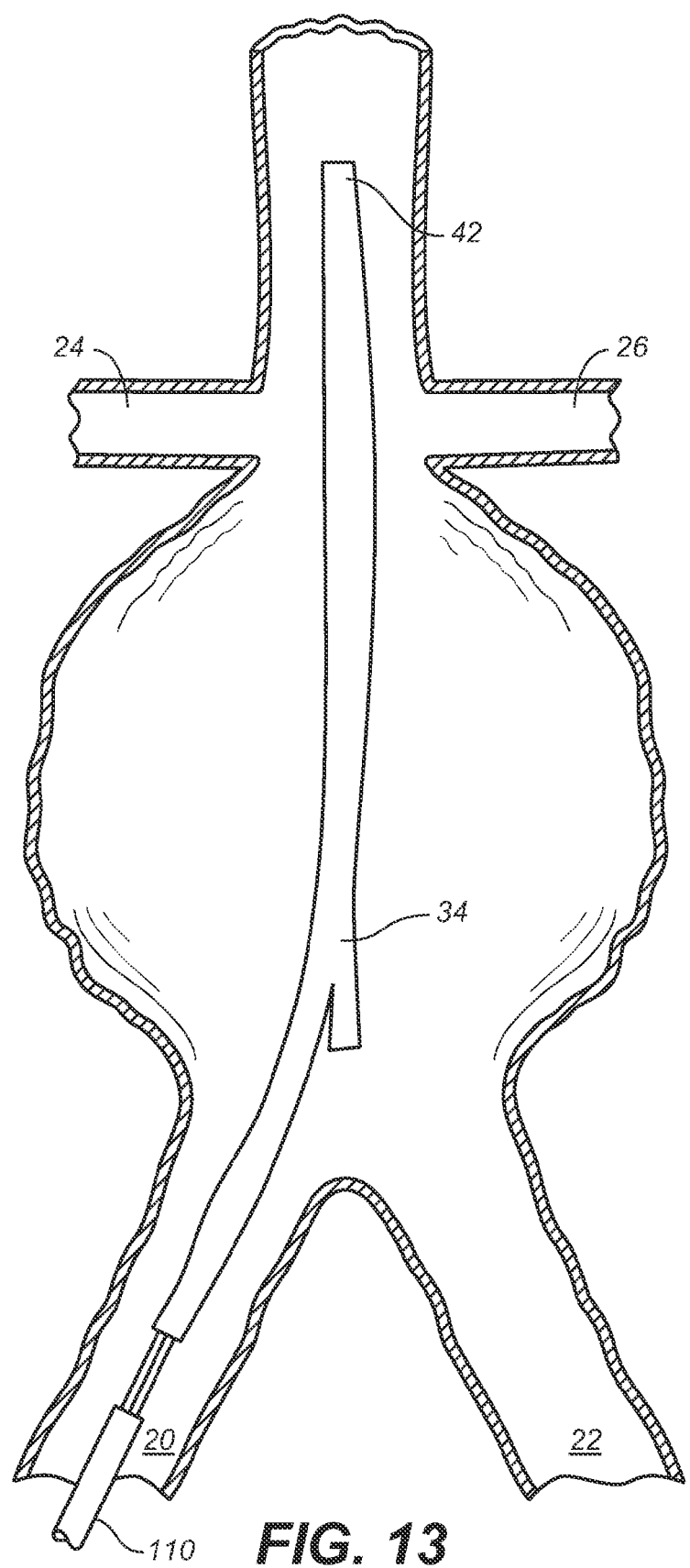
FIG. 13 is a schematic view of the abdominal aneurysmal aorta, having the portion of the exclusion device of FIG. 7 positioned therein prior to expansion of the exclusion device.
Figure 14:
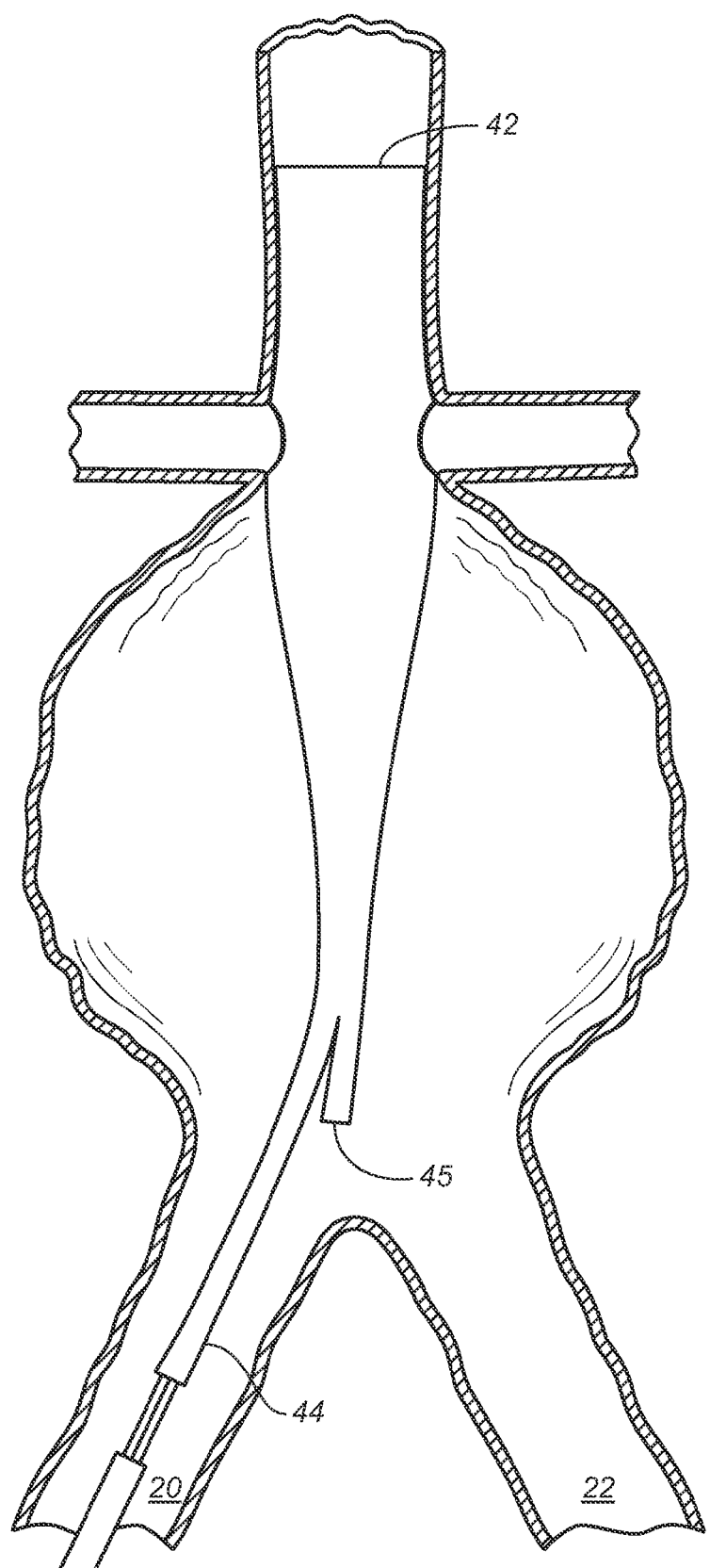
FIG. 14 is a schematic view of the abdominal aneurysmal aorta, showing the exclusion device of FIG. 7 partially expanded and deployed.
Figure 15:
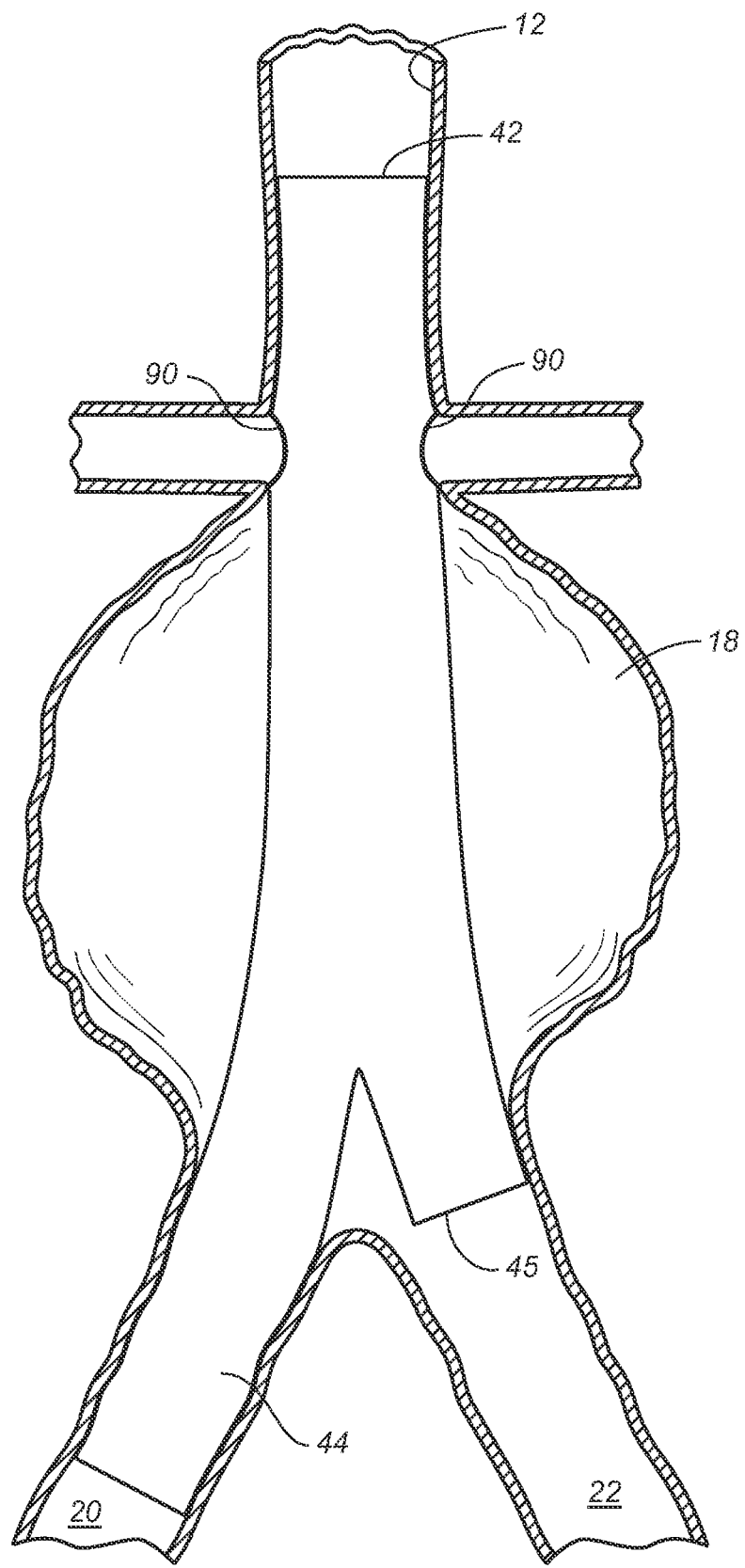
FIG. 15 is a schematic view of the abdominal aneurysmal aorta, showing the portion of the exclusion device of FIG. 7 deployed therein to span the aneurysm.

Referring now to FIG. 10, the initial deployment of the body 34 into the aorta 12 is depicted. Initially, the guidewire 100 is introduced into the body through an incision in the leg, in this instance into the right femoral artery, and the guidewire 100 is tracked to a position such that its end is positioned at a location upstream of the sealing position of the end 42 of the main body 32 against the artery wall 12. The delivery sheath 110 with the tapered tip 114 thereon is then tracked along guidewire 100, until the end 42 of the body 34 is positioned at the intended deployment location, or immediately adjacent to such location, as determined by viewing a fluoroscopic image of the patient at the aneurysmal site 18 in relation to markers on the stent graft body 34, to the position shown in FIG. 11. Thence, the tapered tip 114 can in one configuration be pushed away from the deployment end 112 of the delivery sheath using catheter central member 116, and held away therefrom on the guidewire 110 for later recovery from the patient, as shown in FIG. 12. To begin deployment of the body, the delivery sheath 110 is retracted while holding the body 34 compressed therein stationary, by the use of a stop (not shown) within the delivery sheath which bears against the back of the compressed main body 34 as the delivery sheath retracts around the main body 34. Initially, the end 42 of the main body 34 will emerge from the end 112 of the delivery sheath 110, and thence the portion of the body 34 in which the apertures 51, 53 are located emerges. As the delivery sheath 110 continues to be retracted, the portion of the main body 34 in which the apertures are located is substantially exposed. To position the apertures 90, 92 (FIG. 2) generally in alignment with their respective matching renal arteries 24, 26, the delivery sheath may be rotated and move longitudinally along the artery 12, the longitudinal positioning limited by the need to locate the ends of the body 34 on sufficient healthy tissue to form a sealing engagement with the aorta 12 wall. This may be accomplished in part by partially inflating the balloon 112 to enable fluoroscopic visualization of the relative longitudinal and rotational position of the apertures 90, 92 vis-à-vis the renal arteries. Thence, the delivery sheath 100 may be fully retracted and the balloon 102 inflated to expand the stent framework 36 and press the graft portion 38 into sealable engagement with the aorta wall 12 with end 42 upstream of the renal arteries, seal end 44 downstream of the aneurysmal sac 18 within the iliac branch 20, and also expand the aperture within which the second leg 46 is deployed. Alternatively, a number of balloons may be individually provided to inflate different portions of the main body 34 separately, for example, to enable inflation of end 42 into engagement with the aorta 12 wall before the body is fully withdrawn from the delivery sheath 110. Once body 34 is deployed, the tapered tip 114, delivery sheath 110 and balloon 112 are recovered from the body by tracking the sheath 110 and tapered catheter 116 along the guide wire 100, and the guidewire 100 is then removed leaving main body 34 deployed within the abdominal aorta in a position spanning the aneurysmal site 14 as shown in FIG. 15.

Figure 16:
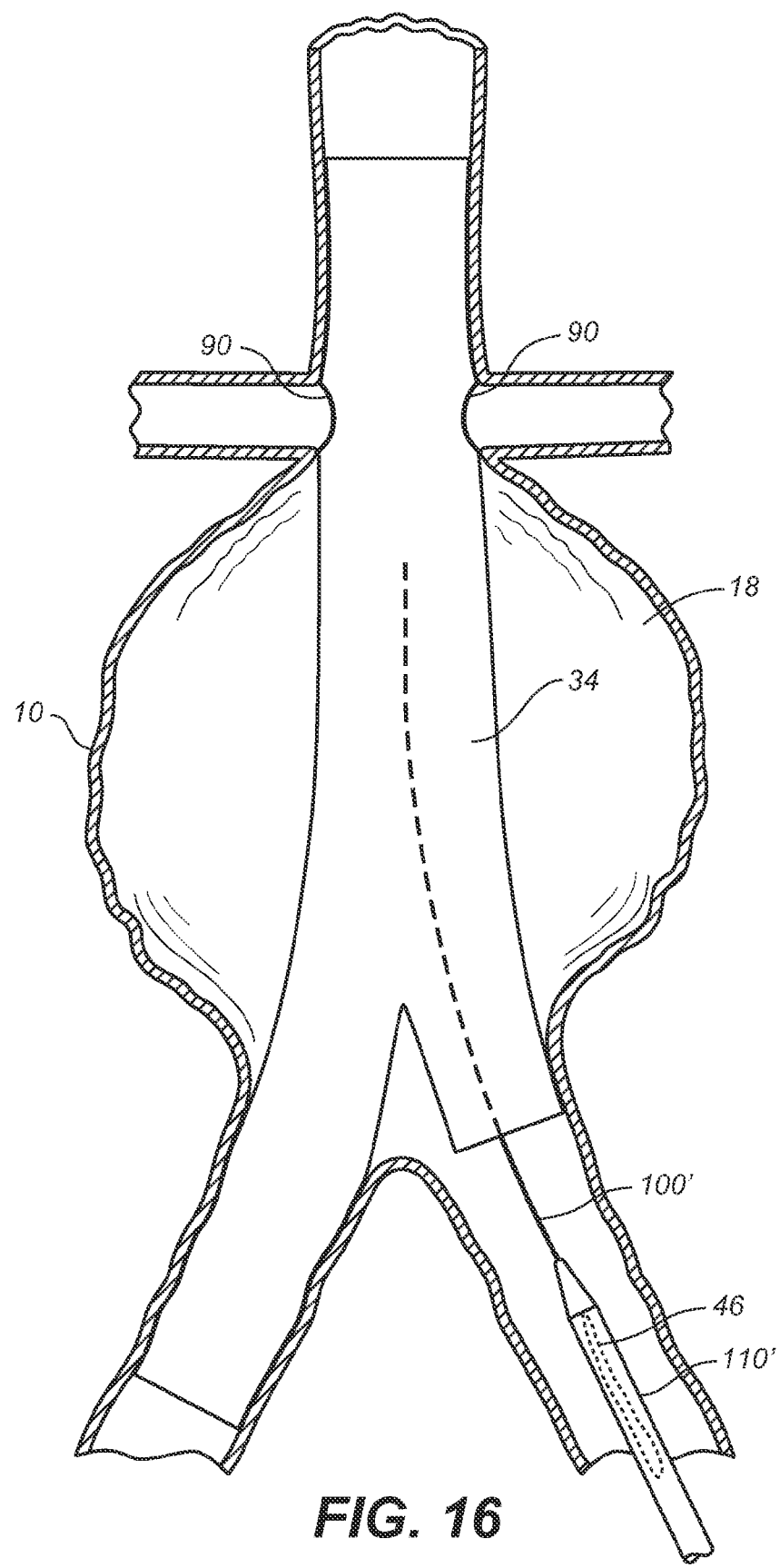
FIG. 16 is a partial schematic view of the abdominal aortic aneurysm of FIG. 1 showing an additional deployment device being positioned to deploy a leg into the portion of the exclusion device deployed as in FIG. 15.
Figure 17:
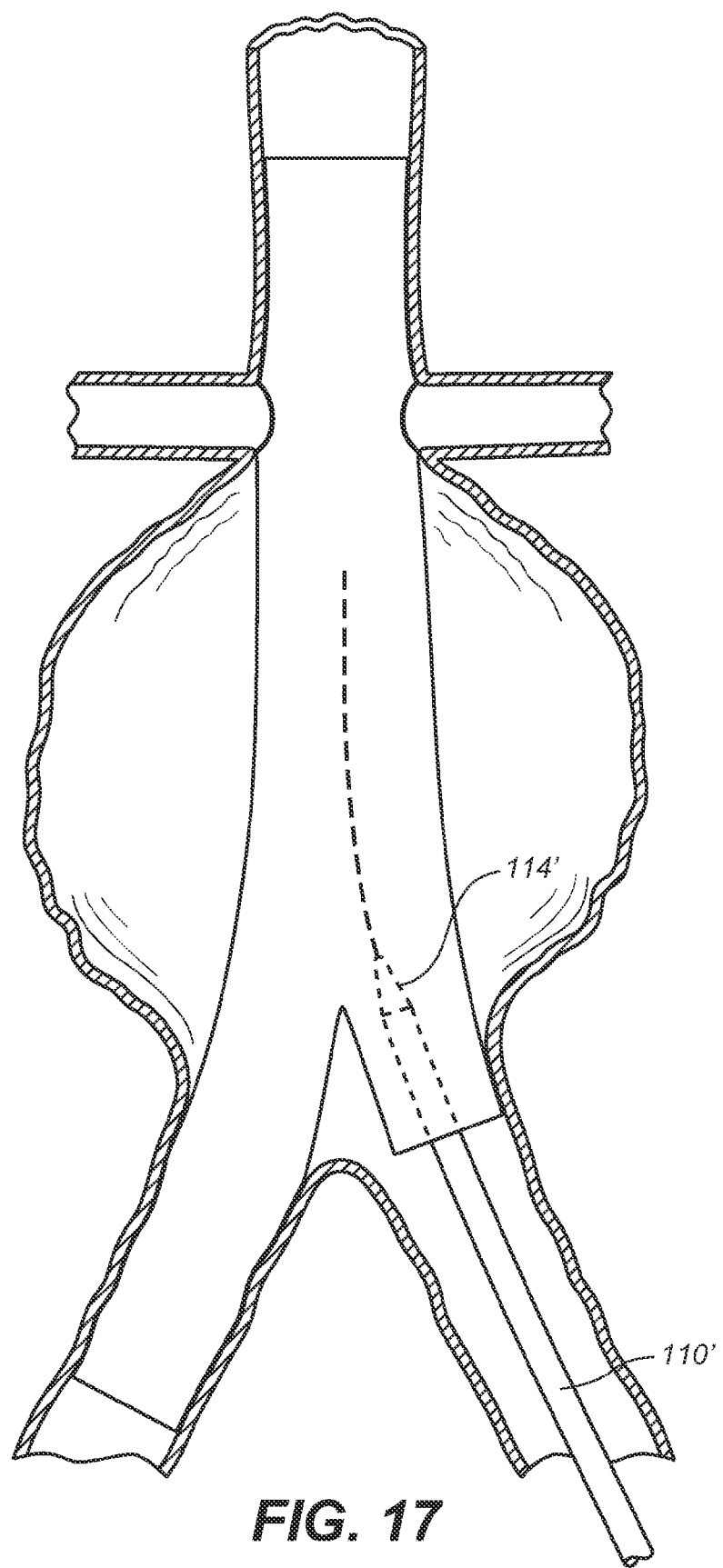
FIG. 17 is a partial schematic view of the abdominal aortic aneurysm of FIG. 1 showing a delivery device in position to deploy a leg into the portion of the exclusion device shown in FIG. 15.
Figure 18:
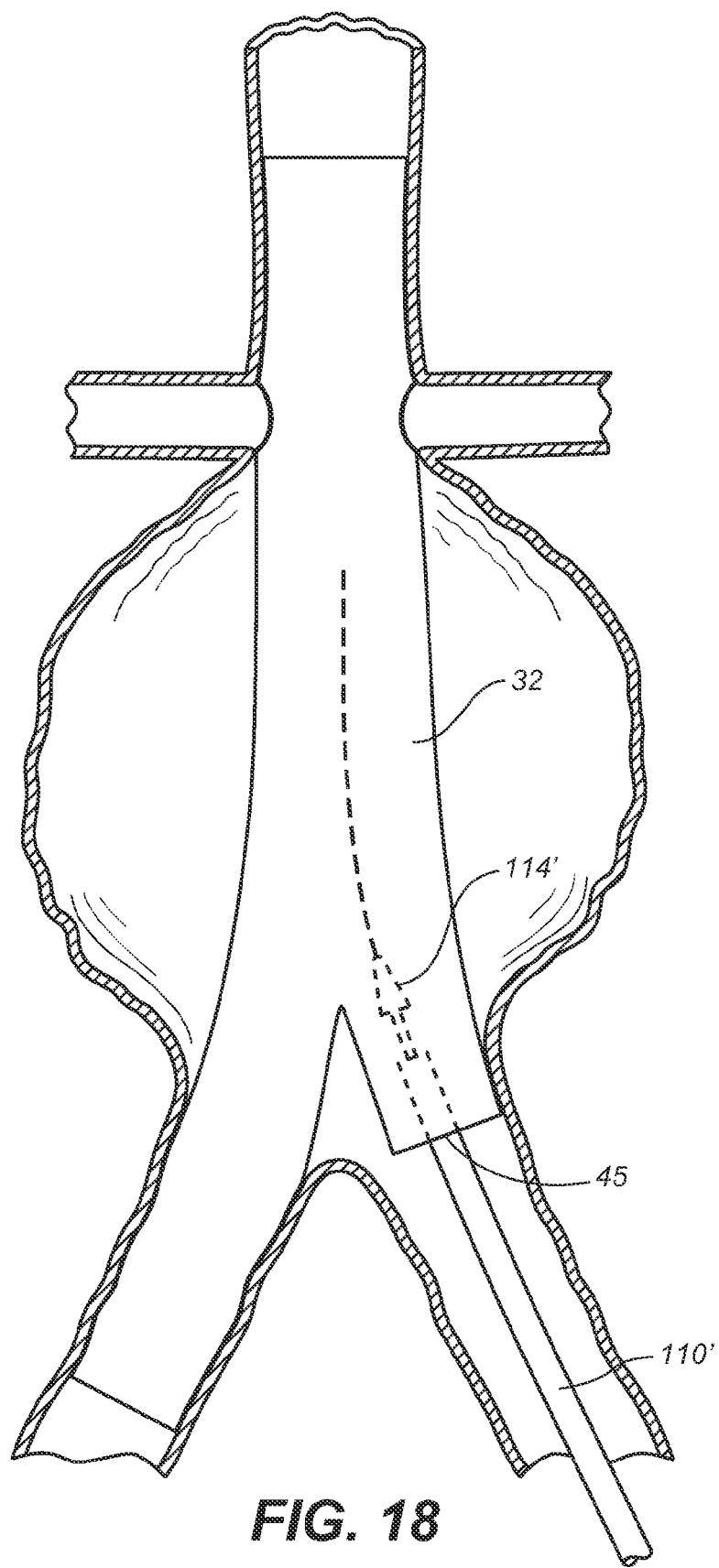
FIG. 18 is a partial schematic view of the abdominal aortic aneurysm of FIG. 1 showing a delivery device prepared to deploy a leg into the portion of the exclusion device shown in FIG. 15.
Figure 19:
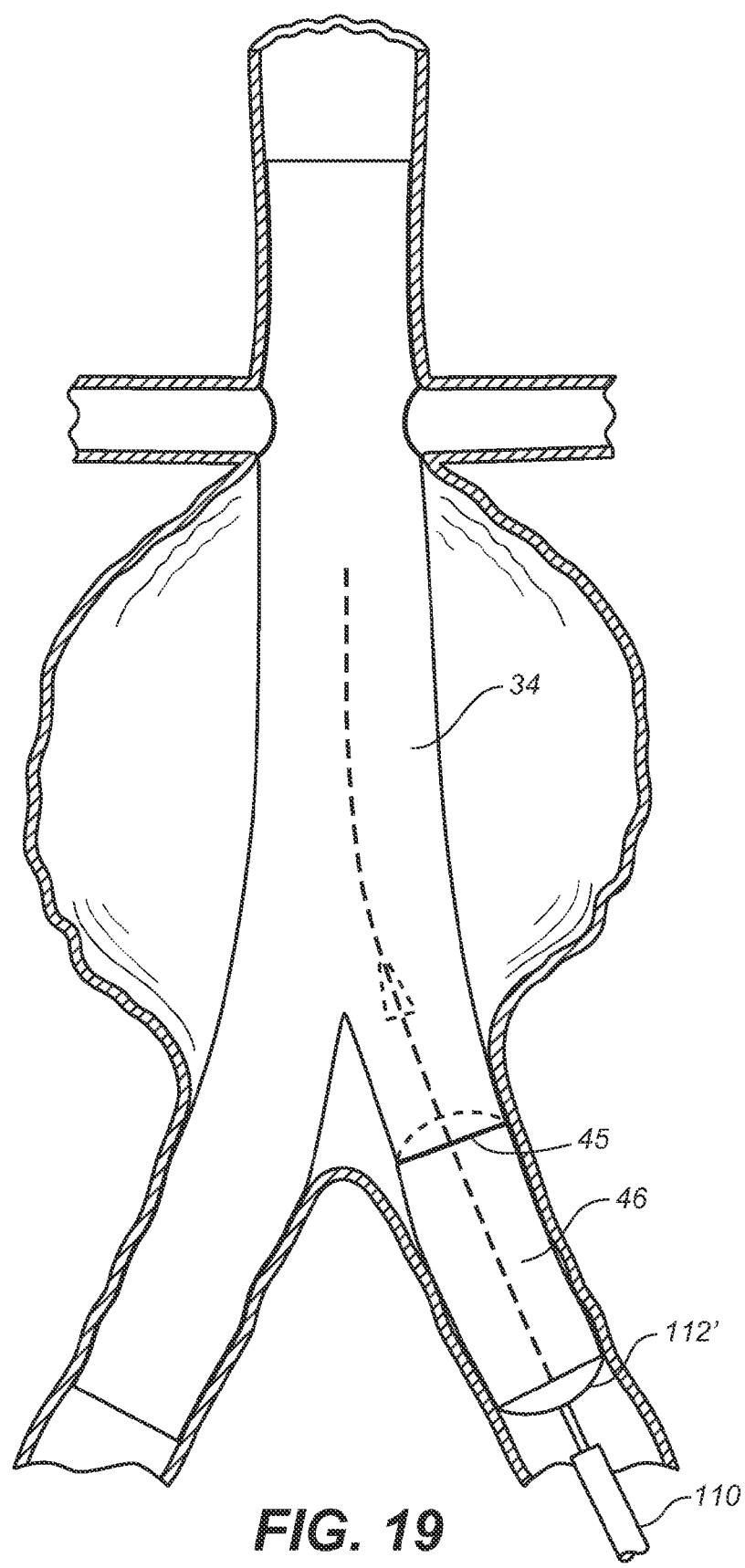
FIG. 19 is a partial schematic view of the abdominal aortic aneurysm of FIG. 1 showing a delivery device deploying a leg into the portion of the exclusion device shown in FIG. 15.

With the main body 34 in place, the second or left or contralateral leg 46 (FIG. 2) must be deployed into leg aperture 45 in main body 34. To provide deployment, a second guidewire 100', is introduced into an incision in the left lag of the patient, and thence guided through the left iliac artery 22 to a position within the main body 34, or extending through the main body 34 previously deployed in the aorta 10, as shown in FIG. 16. Thence, a second delivery sheath 110' of the same general construction as delivery sheath 110, and having the left leg 46 held in a compressed state therein, is tracked along the wire 110' to a position wherein the end of the leg 46 to be deployed within leg aperture 45 is located within the delivery sheath 110' and in a position within the main body 34 where the leg 46 may engage within leg aperture 45 along a sufficient portion of the short leg of the main body 34 surface to form a seal therewith, such position shown in FIG. 17. Thence, the tapered tip 114' is pushed away to expose the leg within the delivery sheath, as shown in FIG. 18. With the leg 46 properly positioned, as verified by radiological markers on the body 34 and the leg 46, the delivery sheath 110' is retracted while the compressed leg 46 is held relatively stationary. Thence, the balloon 112' may be inflated to expand the leg 46 and seal the leg in the leg opening 45 and against the wall of the left iliac artery, as shown in FIG. 19. Once the leg 46 is properly deployed, the balloon 112' is deflated, and the delivery sheath 110', balloon 112 guidewire 100' and tapered tip 114' are removed through the aforementioned incision.

Figure 20:
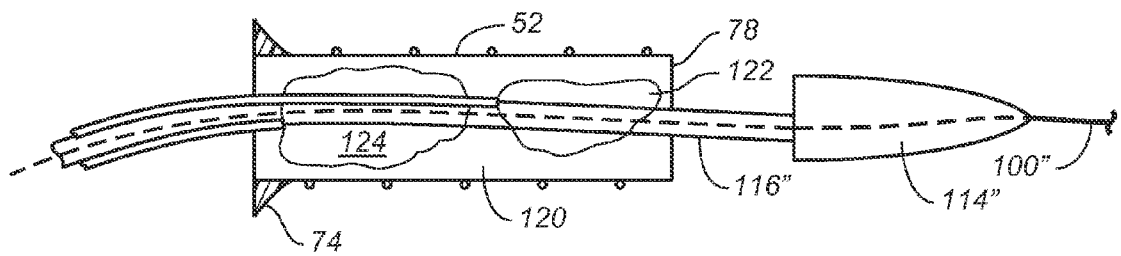
FIG. 20 is a schematic plan view of the renal extension of FIGS. 3 and 4 prepared for and prior to placement in a delivery device.
Figure 21:
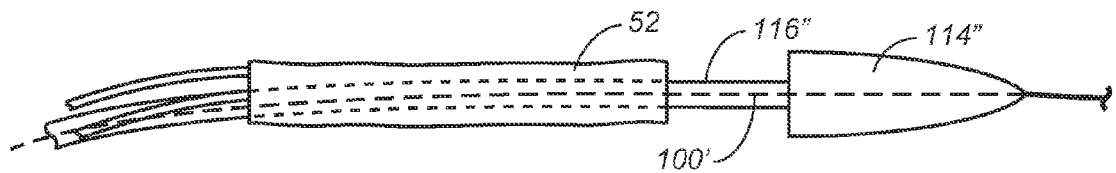
FIG. 21 is a plan view of the renal extension of FIG. 20 compressed for loading into a delivery device.
Figure 22:
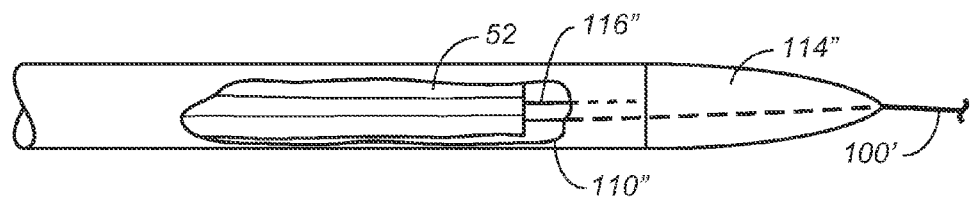
FIG. 22 is a plan view of a delivery device having the renal extension of FIG. 20 compressed therein and ready for deployment into the portion of the exclusion device shown in FIG. 15.

With the body 34 and left leg 46 in place, the renal extensions 50, 52 need to be deployed. Again, prior to deployment, each of the extensions can be compressed over a balloon 120 structure and guidewire 100", and placed into the end of a delivery sheath 110" as shown in FIGS. 20 to 22. During the deployment of the inserts 50, 52, there is a need to expand the inserts 50 or 52 at different positions therein at different sequential times. Therefore, the balloon structure 120 may include a first balloon 122 located within the extension toward the distal end 78 of the tubular portion thereof, and a second balloon 124, separately inflatable from the first balloon 122, is positioned within the insert 52 adjacent the flange 74 as shown in FIG. 20, prior to compression of the insert 52 as shown in FIG. 21 for placement within the delivery sheath 220" (FIG. 22).

Figure 23:
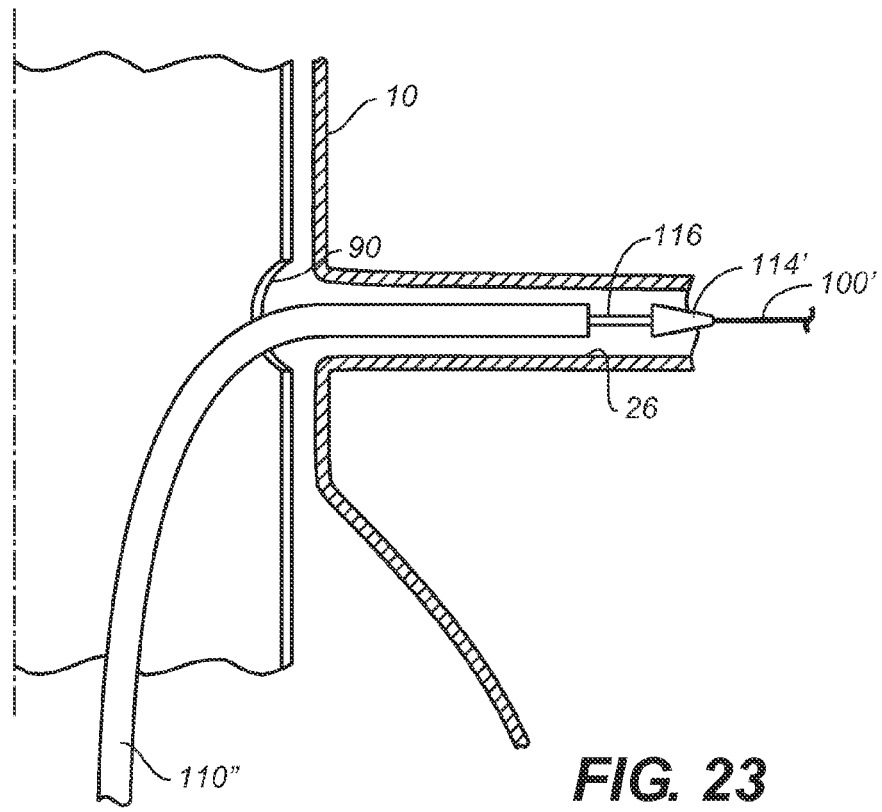
FIG. 23 is partial schematic view of the abdominal aortic aneurysm of FIG. 1 showing a delivery device in position to deploy a renal extension (branch) from a portion of the exclusion device shown in FIG. 15.

To deploy the extension 52, the guidewire 100" is guided through one of the leg incisions and one of the iliac arteries, and directed into one of the renal arteries, in the case of insert 52, renal artery 26. Delivery sheath 110' is then tracked along the guidewire 100", to a position where the renal extension 50 is held in the delivery sheath in a position spanning both the aperture 90 in main body 34 and the renal artery 26 opening as shown in FIG. 23. Thence, the tapered guide 114" is pushed away from the delivery sheath 110", to expose the compressed distal end 78 of renal extension 52 held within the sheath 110" as is shown in FIG. 23. The deployment of the sheath 110" along guidewire 100", and the exposing of the distal end 78 of renal extension 52 held therein, are accomplished in the same general manner as discussed with respect to the deployment of the main body 34 and contralateral leg 46, with the exception that guidewire 100" is directed ultimately into renal artery 26 before the tracking of the delivery sheath 110" thereover to the deployment position of the renal extension.

Figure 24:
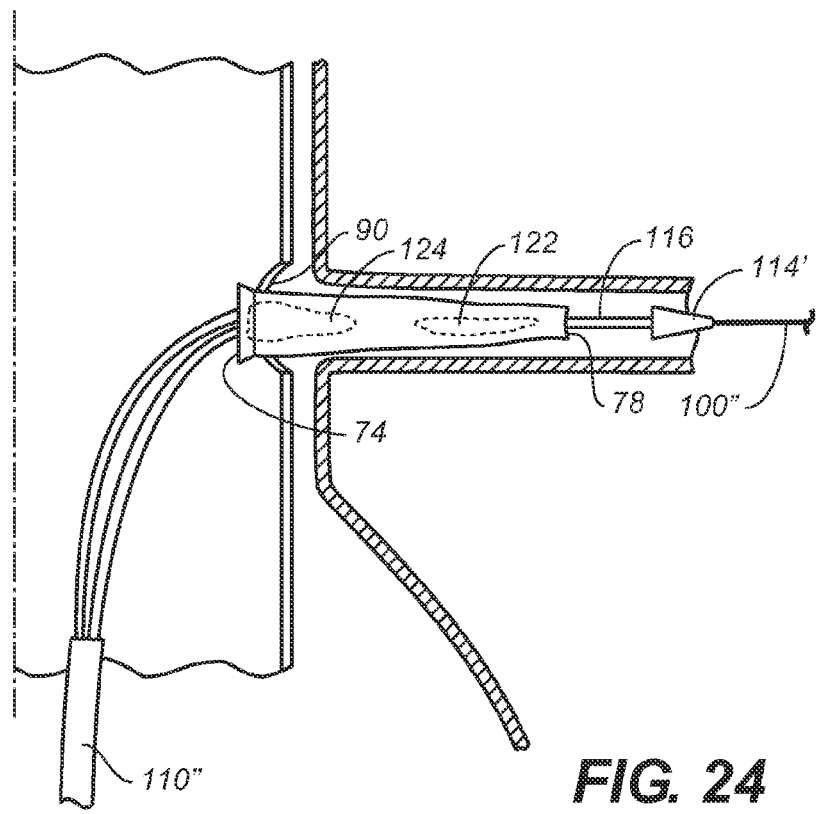
FIG. 24 is a partial schematic view of the abdominal aortic aneurysm of FIG. 1 showing a renal extension deployed from the delivery device and prior to the expansion of the renal extension.
Figure 25:
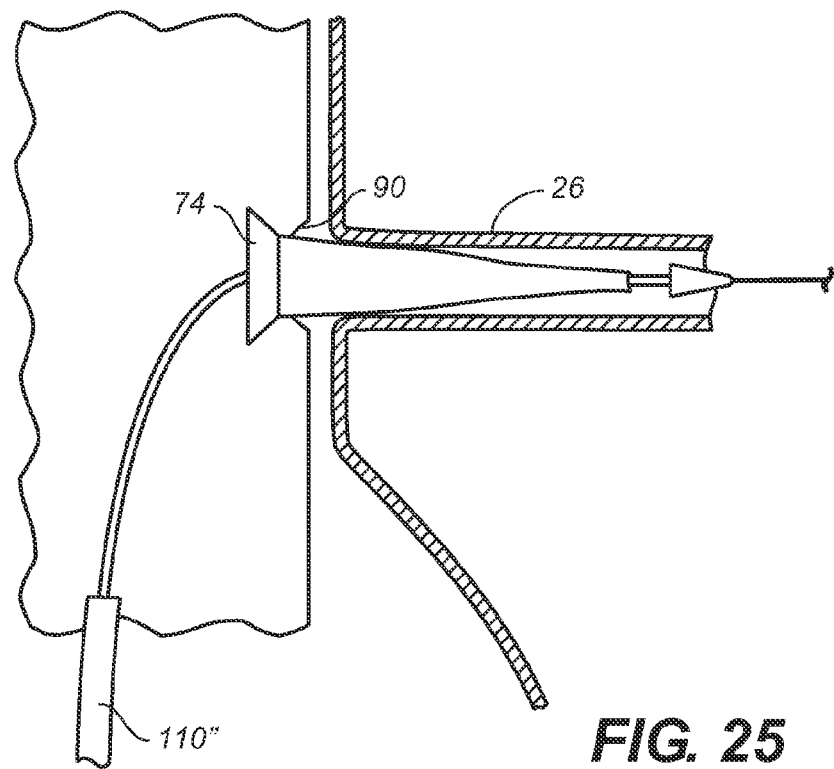
FIG. 25 is a partial schematic view of the abdominal aortic aneurysm of FIG. 1 showing a renal extension partially expanded and extending between the portion of the exclusion device shown in FIG. 15 and an adjacent renal artery.
Figure 26:
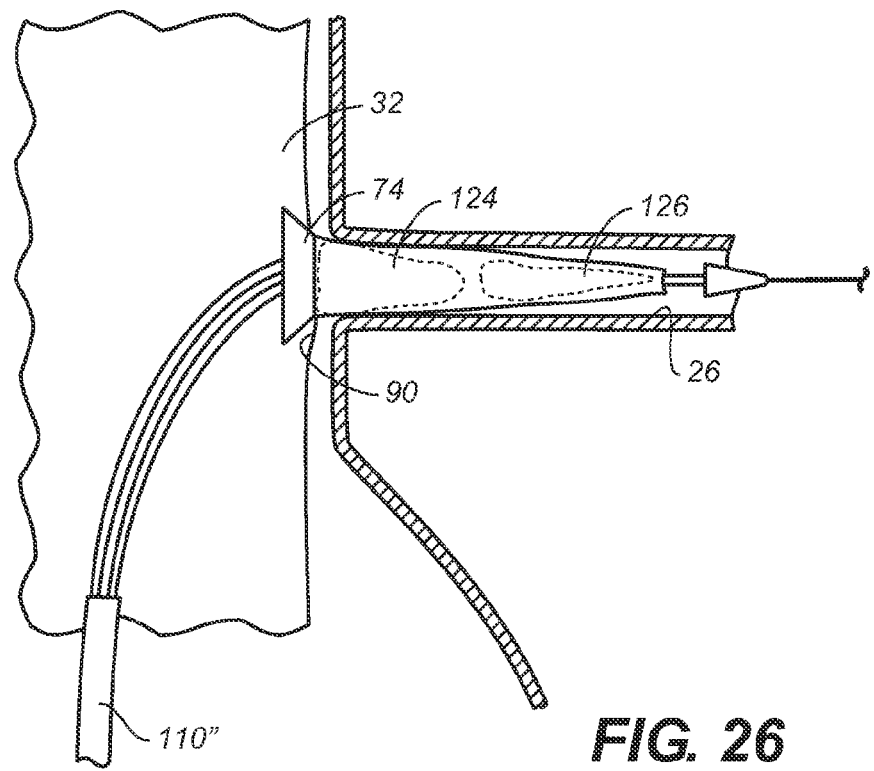
FIG. 26 is a partial schematic view of the abdominal aortic aneurysm of FIG. 1 showing a partially expanded renal extension being positioned to ensure bias between the flange of the renal extension and the body of the portion of the exclusion device shown in FIG. 15.
Figure 27:
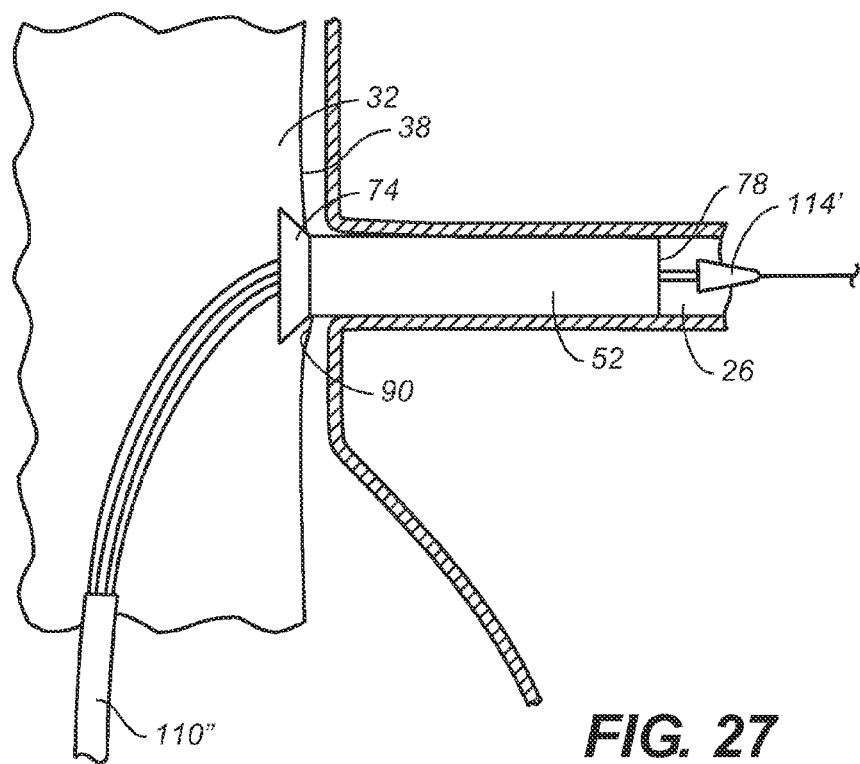
FIG. 27 is a partial schematic view of the abdominal aortic aneurysm of FIG. 1 showing a renal extension fully deployed to span between the portion of the exclusion device shown in FIG. 15 and an adjacent renal artery.

To deploy the renal extension 52, the delivery sheath 110" is fully retracted, such that the renal extension 52 is supported on the guidewire 100" and the balloons 122, 124 as shown in FIG. 24. Based upon the position of the renal extension 52 as the delivery sheath 110" was retracted over it, the flange 74 of renal extension 52 should then be positioned within the aperture 90, and second balloon 124 is inflated, to expand that portion of the renal extension 50 on which flange 74 is formed or supported, such that the outer circumference of the flange 74 is now larger than the circumference of the aperture 90 as shown in FIG. 25. Next, balloon 122 is pushed by pushing on the inflation tubes for the balloons 122, 124, to move the insert 52 toward the opening of the renal artery 26 from the aorta 10 and thereby push the flange 74 against the interior surface of the body 34, and against the perimeter surface of the aperture 90 as shown in FIG. 26, and the first balloon 122 is then inflated to expand the renal extension within the renal artery 26, and thus anchor the renal extension in place in the renal artery 26, while maintaining tension (i.e., a force vector tending to pull the opposed open ends 76, 78 of the insert 52 away from each other) in the extension by virtue of the pushing of the distal end 78 of the renal extension away from the body 34, and deploying the renal extension 52 in the renal artery 26 while maintaining this tension as shown in FIG. 27. With the renal extension 52 deployed, the balloons may be deflated and the balloons 122, 124, delivery sheath 110", tapered tip 114" and guide wire 100 removed from the body. A second such delivery sheath 110" holding renal extension 52 is then tracked along a different guidewire (not shown), to position renal extension 52 in the same fashion as renal extension 50. Thus, when the stent graft 30 is fully deployed, the renal extensions 50, 52 flanges 74 include an outwardly, generally radially vectored (with respect to the tubular axis of the main body 34), load or bias, such that the integrity of the seal between the flange 74 and the apertures 90 against which the flanges 74 of the extensions 50, 52 bear may be enhanced.

Figure 28:
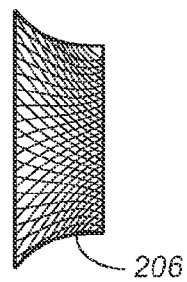
FIG. 28 is a side view of a flange support for supporting a flange portion of a renal extension.
Figure 29:
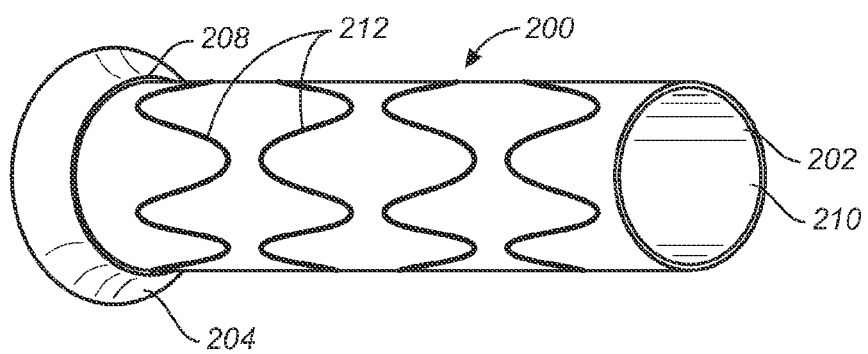
FIG. 29 is an additional configuration of a renal extension.
Figure 30:
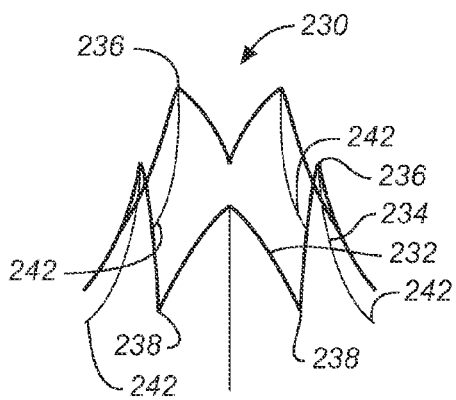
FIG. 30 is a perspective view of a wire basket configured to support the flange of a renal extension.
Figure 31:
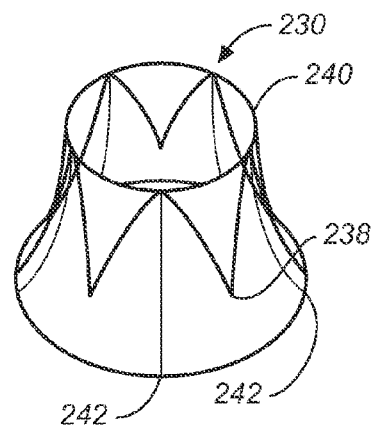
FIG. 31 is a perspective view of the basket of FIG. 30, having additional hoop supports.
Figure 32:
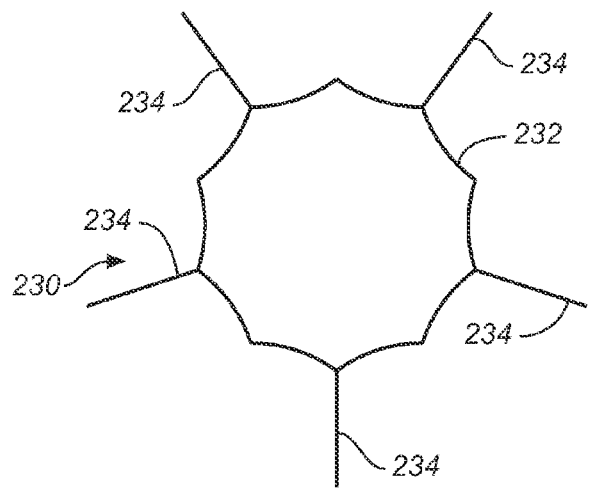
FIG. 32 is a top view of the basket of FIG. 30.
Figure 33:
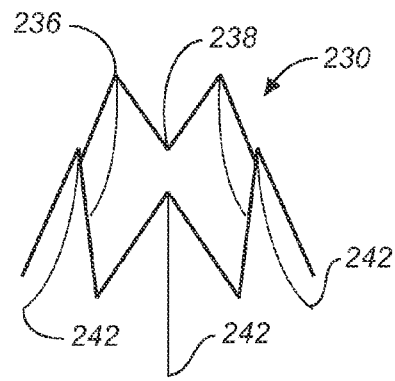
FIG. 33 is a perspective view of an alternative wire basket construction.
Figure 34:
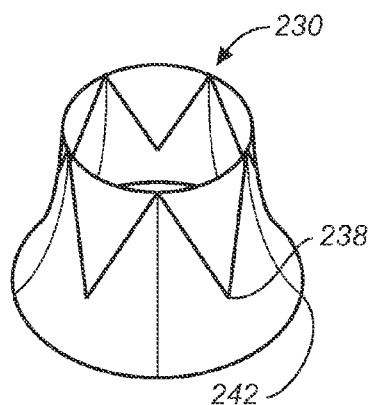
FIG. 34 is a perspective view of the basket of FIG. 33 having additional hoop supports.
Figure 35:
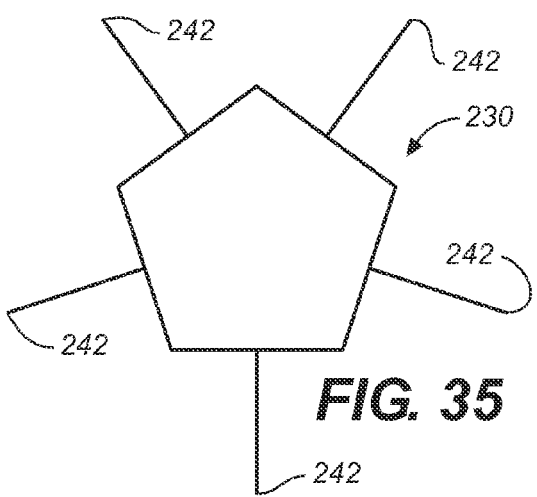
FIG. 35 is a top view of the basket of FIG. 33.

Referring now to FIGS. 28 and 29, an additional construction of the renal extension feature is shown. In this construction, a supported flange renal extension 200 is provided, which is similar in construction and deployed similarly to the inserts 50, 52. However, in this construction, the extension 200 includes a generally tubular extension portion 202, which includes both an excluding material 210 such as Dacron, ePTFE, or other biocompatible material, as well as a stent framework 212 to which the graft material is secured, as was described in relation to the construction of inserts 50, 52, and a supported flange 204 having the same general profile, material and construction as that of the flange 74 of inserts 50, 52, but being supported internally by a support feature. The support feature may be a generally frustroconical (in the free state) wire mesh 206 (FIG. 28), constructed of generally overlapping wires such as is present in a screening material, which mesh 206 is encapsulated within a biocompatible polymer such as silicone by dipping the mesh 206 in a liquid precursor of the polymer and removing the mesh, repeatedly, until a thin film of the polymer of the order of 1 to 2 mm is formed over the mesh 206 (over molding) (and may also be adhered to the adjacent region of the tubular extension portion 202). Additionally, the wire mesh 206 may be held in an insert mold, and silicone polyurethane, polyurethane blends, polyurethane alloys, ePTFE, PET, polypropylene, polyethylene or other biocompatible materials molded thereover. Alternatively, the mesh 206 may be covered with graft material such as that used in the fabrication of tubular extension portion 202. The supported flange 204 may be secured to one end of the tubular extension portion 202 such as by sewing the mesh 206 to one end 208 of the tubular extension portion 202, or by extending the stent framework 212 of the tubular extension portion 202 to form the wire mesh 206 integrally therewith, or other mechanisms. The wire mesh 206 provides rigidity to the supported flange 204, to help ensure that upon and after deployment of the supported flange 204 in the same generally procedure as that of the flange 74, the supported flange will not be extruded or otherwise pulled or pushed through an aperture in the main body of a stent graft into which it is deployed. The mesh 206 may be configured from a stainless steel wire of a diameter of approximately 0.10 to 0.50 mm diameter, in which case a balloon must be used upon deployment of the extension 200, to open the supported flange 202 against the inside of the main body 34 of a stent graft, or of a shape memory material, such as nitinol, in which case the mash 206 will regain its original shape after release from a delivery sheath at the deployment location. The mesh 206 may also be formed by laser cutting a frustroconically shaped thin steel, nitinol, or other support material to create a mesh. Again, as in the case of the renal extensions 50, 52, by first deploying and securing the distal end of the cylindrical renal extension into the renal artery before releasing the supported flange 204 within the main body 34 of the stent graft, the supported flange 204 may be employed to pull the body portion, about the aperture within which the supported flange renal extension 200 is deployed, in the direction of the artery wall, thereby ensuring a sealing engagement between the supported flange 204 and the main body 34 of the stent graft at the aperture through which the supported flange renal extension 200 extends.

Alternatively, in place of a wire mesh, the support feature may include a wire basket, such as that shown in FIGS. 30 to 35, configured of a metal wire having a diameter on the order of one mm or less. Preferably, the basket is formed by laser cutting a tubular or frustroconical tubular sheet of a metal such as stainless steel or nitinol, to leave behind a shaped wire outline. In this construction, the wire basket 230 includes a first support framework 232 configured of a generally zig-zag configuration extending in a generally outwardly curving or spreading, cylindrical profile, and a plurality of spreader wires 234, each extending from a terminal apex of the first support framework, and likewise extending laterally and along a generally outwardly curving or spreading profile. In the construction of the wire basket 230 shown in FIGS. 30 to 32, the wires of the first support framework 232 in addition to follow a generally outwardly curving or spreading profile, also have an arcuate shape in the circumferential direction of the basket, i.e., the distance between an adjacent set of wires extending between two spreader wire decreases at a rate greater than a linear rate as the distance from the small diameter apex 236 to the larger diameter apex 238 is spanned. Alternatively, in the construction shown in FIGS. 33 and 35, this relationship is linear. If greater support rigidity or support is desired for the basket to help provide structural support for the flange to be molded thereover, an additional wire hoop 240 can be provided to connect between the smaller diameter apexes 236 of the basket 230 as well as a second hoop 244 may be provided to connect the distal ends 242 of the spreader bars 234. This modification is shown for the basket of FIGS. 30 and 32 as FIG. 31, and for the basket of FIGS. 33 and 35, as the basket of FIG. 34. As with the construction of supported flange 204, a flange having an internal support is constructed by dipping the basket 230 in a polymer, such as silicon polyurethane, polyurethane blends, polyurethane alloys, ePTFE, PET, polypropylene, polyethylene or other biocompatible materials, so a web 246 of polymer is formed over the wire basket 230 as shown in FIG. 36. The wire basket 230 is secured to an extension 250 such as by sewing the wire basket to the graft material 252 of the extension, sewing, welding or otherwise connecting the wire framework of the basket to the stent framework 254 of the extension, or otherwise interconnecting the structures as shown in FIG. 37. The polymer web may be formed by dipping the wire basket 230 in a liquid polymer and pulling it out to leave a thin continuous web of polymer extending between the basket wire elements, or insert molding a polymer over the basket. Additionally, a graft material may be sewn or otherwise affixed to the wire basket to form a sealing surface. The wires constituting the wire basket 230 may be configured or a biocompatible metal such as stainless steel, in which case the basket and flange provided therewith must be expanded, in situ, to bring the web 246 into sealing engagement with the body 34 of a stent graft at an aperture therethrough 90, 92 as was shown and described with respect to FIGS. 20 to 27 hereof. Alternatively, the wire material comprising the wire basket 230 may be a shape memory material, such as Nitinol, wherein the flange formed by the basket 230 and web 246 will self expand when released from a delivery sheath in situ.

The wire basket 230 configuration provides a continuously, outwardly curving, sealing surface 248 provided by the web 246 which is readily alignable and receivable within the apertures 90 of the body 34 of the stent graft. Thus, when the supported flange insert 260 of this construction is deployed as shown and described with respect to inserts 50, 52, the supported flange formed of the web 246 may be pressed against the interior surface of the body 34 of the stent graft about the apertures 90, 92.

Referring now to FIGS. 38 and 39, yet another construction of an extension for a branch artery is shown, again specifically, a renal extension for placement into the main body 34 of the stent graft as described with respect to FIG. 7 to 19 hereof. In this construction, a dual flange extension 300 is shown, such that a first flange 302 is provided for placement within the tubular body 34 of a stent graft, and a second flange 304, (or alternatively an enlarged diameter ring such as might be described as a circular ring or bump or ridge) from which the tubular body 306 of the extension extends, is provided to seal about the aperture 90 on the exterior surface of the main body 34.

Extension portion, in one aspect of this construction, includes a generally tubular extending portion 310, which may be provided from a Dacron or other biocompatible cloth, a polymer sheath, or other biocompatible material which may be formed into a tubular conduit which is capable of substantially preventing blood flow therethrough, and which can effect a seal between a graft material and adjacent wall portions of an artery, such as renal artery 24 or 26. The tubular material is supported by attachment thereof to a stent framework 312, comprised of a plurality of individual stents 314. The tubular extending portion 310 terminates at a distal end 316, at which the outer surface of the tubular portion 310 may engage against the renal artery 24 or 26, and a proximal end 318, which is received within or otherwise affixed to a double flange portion 320 comprising the first flange 302 and second flange 304.

Figure 40:
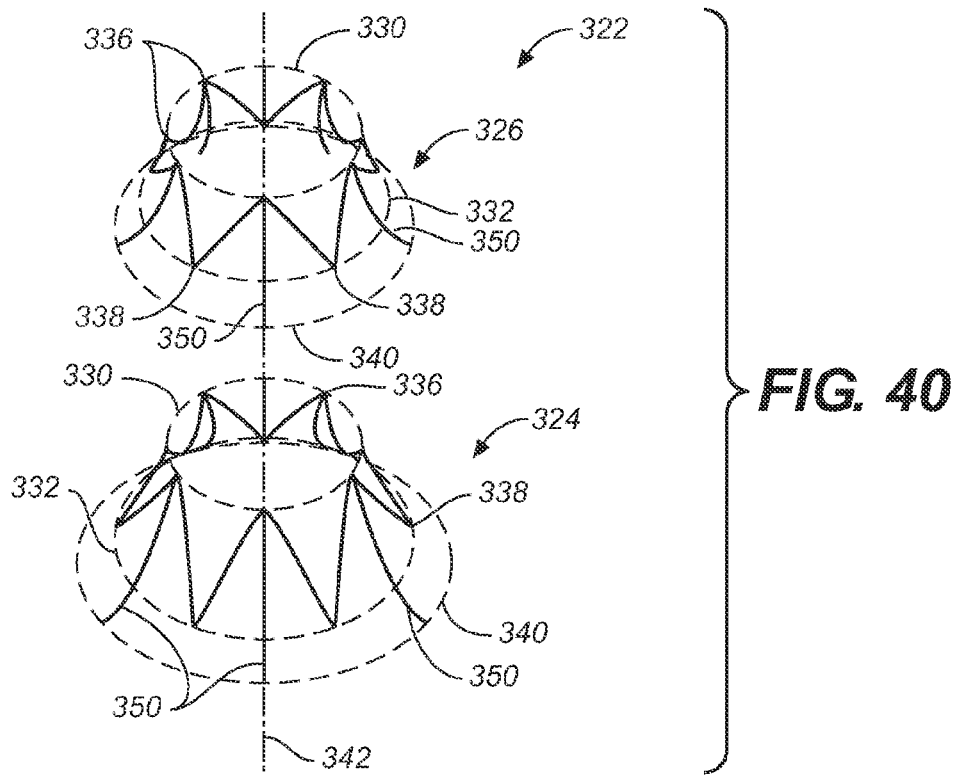
FIG. 40 is a perspective view of a wire basket support for the double flange of the renal extension of FIG. 38.

Referring now to FIG. 40, the supporting structure of the double flange portion 320 is shown in detail. Specifically, double flange portion 320 includes a first support basket 322 which is molded or otherwise secured within first flange 302 and a second support basket 324 is provided and molded or otherwise secured within second flange 304. Each of baskets 322, 324, are generally configured by laser cutting tubular or frustroconical tubular sections of metal, such as stainless steel or nitinol, such that a first hoop portion 326 is configured in a zig-zag configuration and has a diameter on the order of less than 0.50 mm, having a minor imaginary diameter 330 (shown in phantom) and a larger intermediate imaginary diameter 332 (Shown with dashed lines.) The zig zag configuration includes opposed apexes, such a plurality of first apexes 336 are located at the minor imaginary diameter 330, and second apexes 338 at the intermediate imaginary diameter 332. Additionally, each zig zag cycle follows a profile which follows a generally increasing curvature from the first imaginary diameter 330 to the intermediate imaginary diameter 332. At each apex 336, a rib 350, comprising a length of laser cut metal connected to the apex 336, extends from the first imaginary diameter 330 to a second imaginary diameter 340, the curvature of the rib as it extends between the first and second general diameter following the same general profile as the curvature of the zig zag portion, and also being aligned generally along a plane collinear with the centerline 342 of the baskets 322, 324. The second imaginary diameter 340 is larger than the intermediate imaginary diameter 332, which in turn is larger that that of first imaginary diameter 330. Each rib 350 has a length which is longer that the span of the zig zags in the centerline 342 direction. The first imaginary diameter 330 and intermediate diameter 332 of the second basket portion 324 are of the same approximate diameter as the first basket 322 however, the second imaginary diameter 340 is larger in the second basket 324 as compared to the first basket 322, and the ribs 350 of the second basket 324 is longer than that of the ribs 350 of the first basket.

To form the double flange portion 320, the two baskets are held in an insert mold, and a thin film of silicon, polyurethane, polyurethane blends, polyurethane alloys, ePTFE, PET, polypropylene, polyethylene or other biocompatible materials is formed thereon as a web 352 as shown in section in FIG. 39. To provide relative positioning between the baskets 322, 324, and to secure the baskets 322, 324 and the tubular extension portion 310, the tubular extension portion 310 may be secured, at its proximal end 318, to the second basket 322 where the apexes 336 occur at the first imaginary diameter 330, such as by sewing the graft material 310 or the stent frame 312 thereto before the baskets 322, 324 are loaded into a mold for molding a thin polymer layer thereover (over molding). Wire baskets 322, 324 and stent framework 312 may be configured of stainless steel or other biocompatible metal, or of a shape memory material, such as Nitinol. Once the molding is completed, the resulting flanges 302, 304 include an outwardly extending curving upper face 311, and a similarly outwardly extending lower face 313, that join at a tip 315. Upon deployment, the lower face 313 of the second flange 304 will be engaged over, and preferably against, the outer surface of body 34 about the perimeter of aperture 90, and the inner face 311 of the first flange 302 will be deployed against the inner surface of the body 34 about the circumference of the aperture 90.

Referring now to FIGS. 41 to 49, the deployment of a double flange extension 300 having either a shape memory material support structure or a non shape memory support structure are shown separately. In each case, the double flange extension 300 is deployed into an aperture 90 in a previously deployed body 34 of a stent graft as was deployed such as by the methodology shown and described with respect to FIGS. 7 to 19 hereof.

Figure 41:
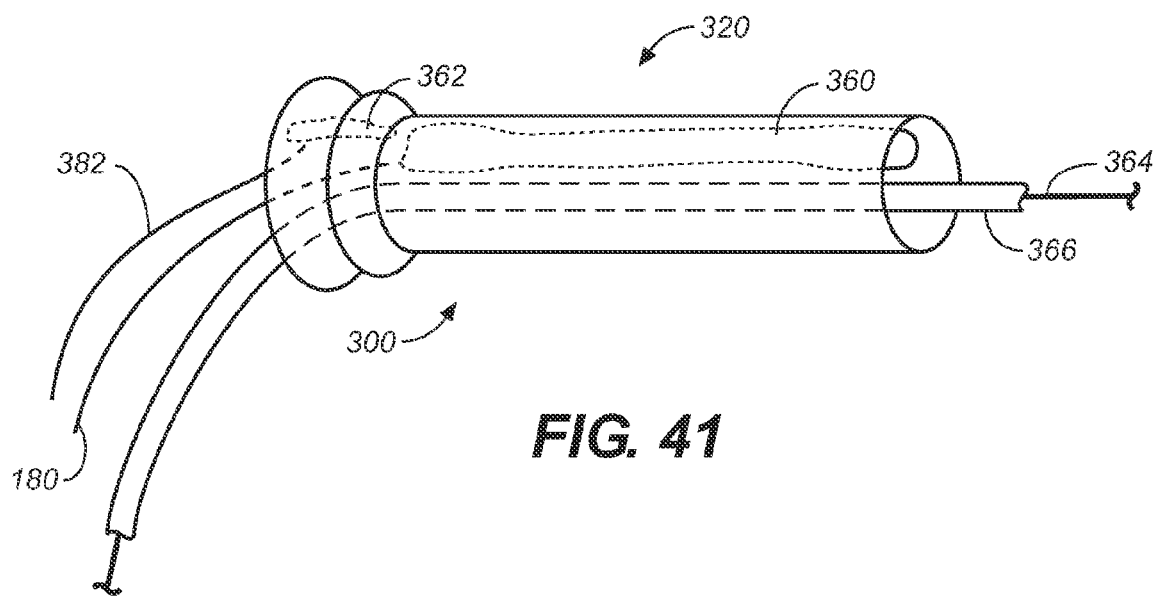
FIG. 41 is a perspective view of a renal extension being prepared for placement in a delivery device.
Figure 42:
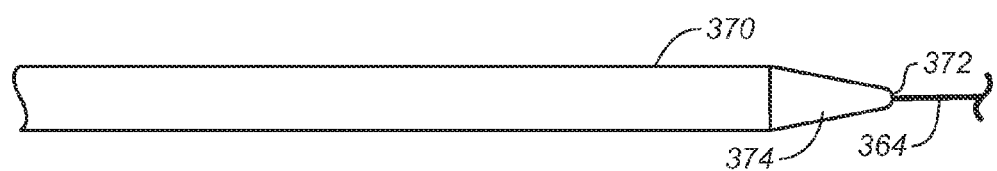
FIG. 42 is a plan view of a delivery device for deploying the renal extension of FIG. 38.

Referring initially to FIGS. 41 to 45, the deployment of a non-shape memory supported double flange extension 300 is shown. In this deployment paradigm, the body of the double flange extension 300, including both the tubular extension portion and the double flange portion 320 must be expanded by a device such as a balloon. Thus, as is shown in FIG. 41, the double flange extension 320 is held in its deployed shape, and a first balloon 360 is loaded within the tubular extension portion 310 such that it extends from the distal end 318 of the extension to the interior of the first flange 302. A second balloon 362 is provided adjacent to the first flange 302. A guidewire 364, and a tapered catheter center member 366, are extended through the extension 320. The extension 320 then is compressed, over the balloons 360, 362 and the wire 364, catheter 366, and the compressed extension is then loaded into the open end of a sheath 370 (FIG. 42) for the deployment of the extension 320 into the body 34 and adjacent renal artery 24 or 26. Typically, the guidewire 364, catheter 366 and balloon lines 380, 382 for supplying air or other gas under pressure to the balloons 360, 362 respectively, are previously passed through the length of the sheath 370 before the extension is compressed and passed into the open end of the sheath 370. The guidewire 364 is also passed through a central aperture 372 in a tapered tip 374, the end of catheter 386 is affixed to the tapered tip (not shown), and the tapered tip pushed against the open end of the sheath 370 as shown in FIG. 42. Additionally, a stop (not shown) is provided within the sheath 370, which may be held stationary when the sheath 370 is retracted, to hold the double flange extension 300 generally stationary when the sheath 370 is retracted. The double flange extension 300 (without shape memory support) is now ready for deployment in a stent graft body 34 previously deployed at an aneurysmal site 14 in an aorta 10 as shown in FIGS. 7 to 19.

Figure 43:
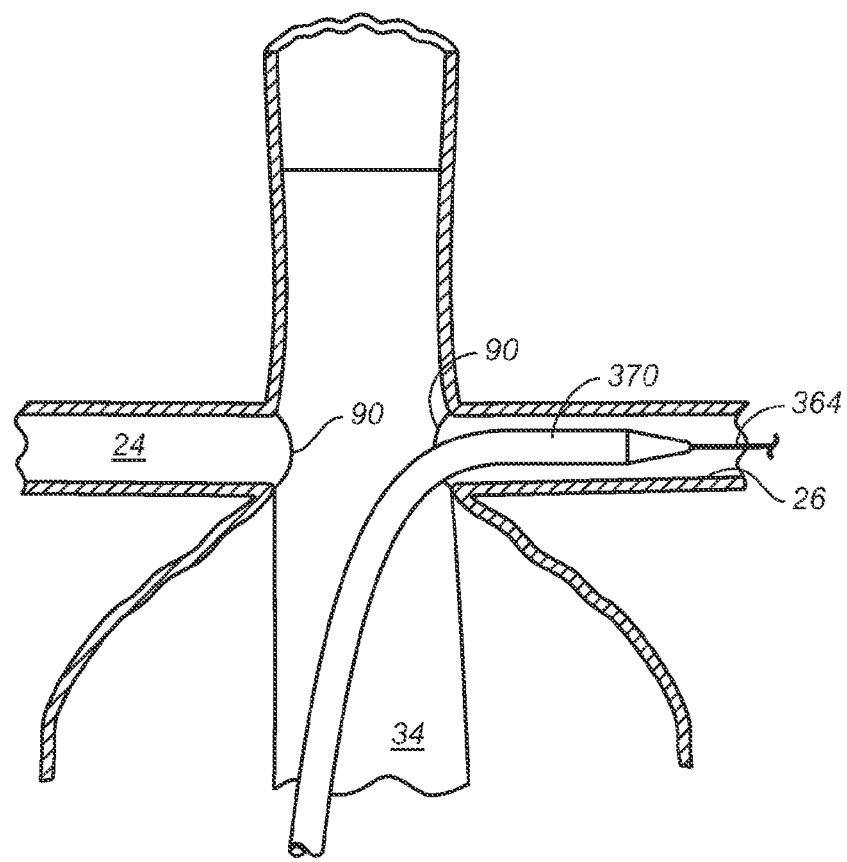
FIG. 43 is a partial schematic view of the portion of the exclusion device and adjacent aorta of FIG. 15, showing the positioning of the delivery device of FIG. 42 therein in position to deploy the renal extension of FIG. 38.

Referring now to FIG. 43, the sheath 370 is shown extending into a renal artery 26, having been tracked over the guidewire 364 which was passed through the previously deployed body 34 and through an aperture 90 thereof and thence into renal artery 26. The position of the double flange extension 300 therein, and in particular the location of each of the first and second flanges 302, 304 vis a vis the aperture 90 are visualized fluoroscopically, to ensure that second flange 304 is disposed to the exterior of body 32, and first flange 302 is deployed interiorly of the cylindrical body 32. The fluoroscopic visualization may be enhanced by locating radiological markers at the flanges 302, 304, such that, when the sheath 370 is retracted as is shown in FIG. 44, the still collapsed or compressed double flange extension 300 is positioned such that first flange 302 and second flange 304 are located adjacent to the aperture 90 in the body 34 of the stent graft.

Figure 44:
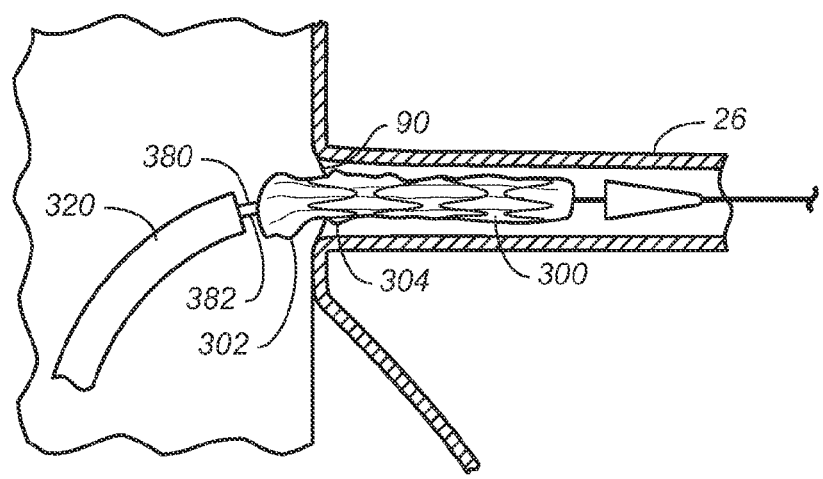
FIG. 44 is a partial schematic view of the portion of the exclusion device and adjacent aorta of FIG. 15, showing the renal extension of FIG. 38 in position to be expanded into a final placement position.
Figure 45:
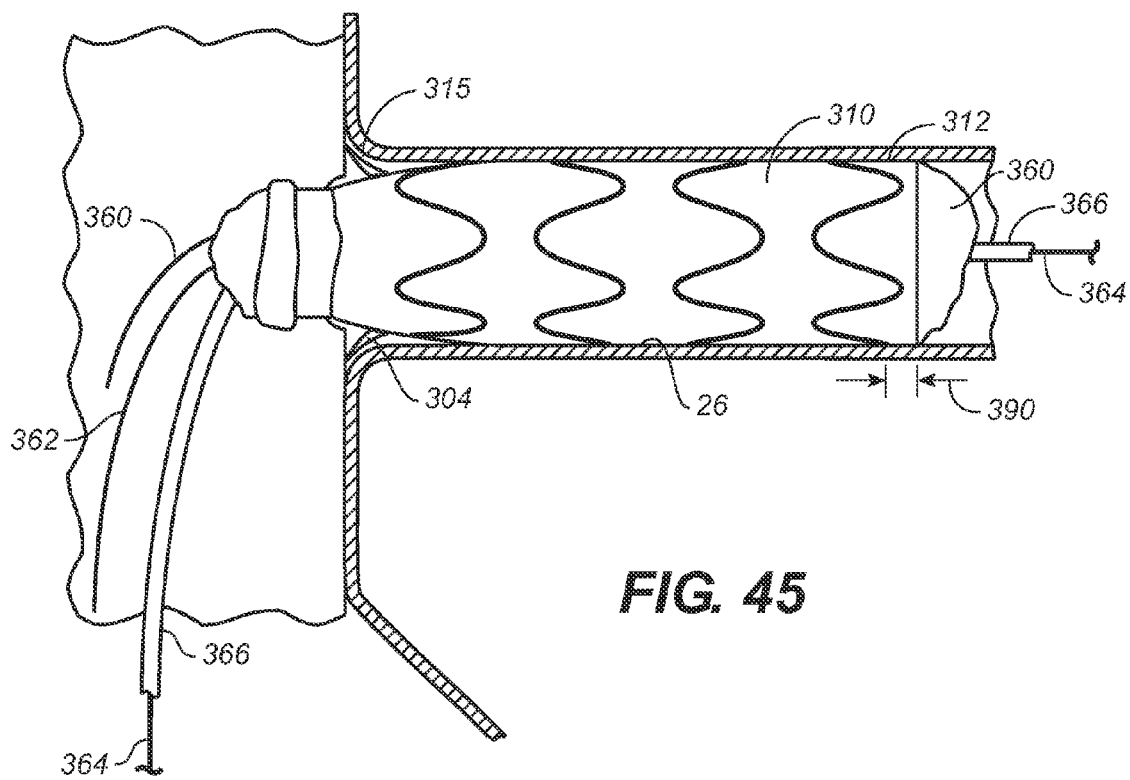
FIG. 45 is a partial schematic view of the portion of the exclusion device and adjacent aorta of FIG. 15, showing the renal extension of FIG. 38 partially expanded into a final placement position.

Once the double flange extension 300 is properly positioned, and the sheath 370 withdrawn as shown in FIG. 44, the double flange extension 300 is supported in renal artery 26 on wire 364, catheter 366, and inflation lumens 380, 382, and the relative position of the extension 300 may be manipulated by moving these elements. Then, as shown in FIG. 45, the surgeon may pressurize lumen 380 to inflate balloon 360, thereby expanding the tubular extension portion 310 such that the portion of the tubular extending portion 310 inwardly of end 312 pushes against, and seals against, the inner wall of renal artery 26, and the second flange 304 is partially expanded such that the tip 315 thereof is annularly disposed adjacent to, and of a larger diameter than, the aperture 90. Again, as with the single flange embodiments of the extending portion shown and described herein, the double flange extension 300 may be deployed such that the flanges will result in a generally radially outwardly loading of the wall of the main body 34 at the aperture 90, by locating the end 318 of the extension 300 slightly offset outwardly from the body by an offset amount 390, which is selected to ensure that upon expansion of the flanges, the first flange 302 will expand against and outwardly bias the body 32 about the aperture 90, yet the second flange 304 will be fully deployed outside of the main body 32.

Figure 46:
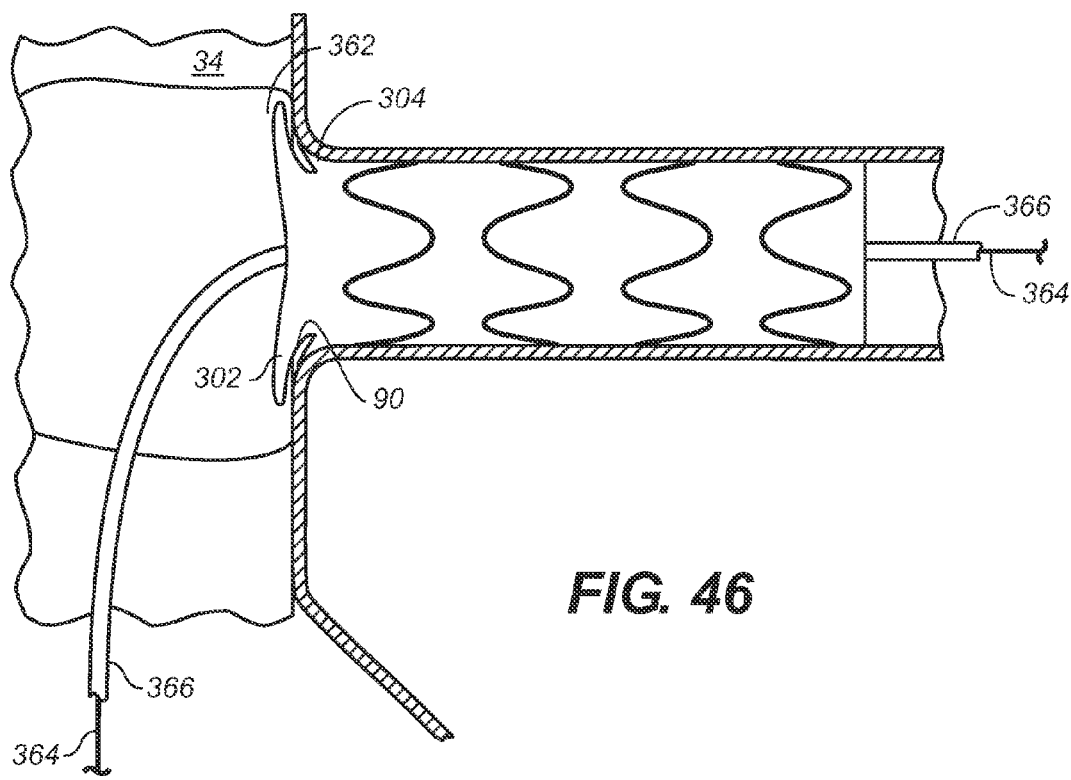
FIG. 46 is a partial schematic view of the portion of the exclusion device and adjacent aorta of FIG. 15, showing the renal extension of FIG. 38 expanded into a final placement position spanning from the portion of the exclusion device and into the adjacent renal artery.

Once the double flange extension 300 is substantially expanded, as shown in FIG. 45, the balloon 360 is deflated, and balloon 362 is inflated as shown in FIG. 46, which causes first flange 302 to be expanded and fully expand the flange region of the double flange extension 300, and thereby fully expand second flange 304 over the exterior of the aperture 90, while inner flange 302 pushes against the interior surface of body 32. This causes a pinching type positioning of the portion of body 32 about the aperture 90, i.e., the expansion of the inner flange pushes the inner and outer flanges 302, 304 against each other, with that portion of the body 32 surrounding the aperture 90, to affect sealing of the aperture 90 from both the interior and exterior of the aperture 90 as is shown in FIG. 46. Thence, the balloon 362 is deflated, and the delivery elements, including sheath 370, tapered tip 374, wires 364 and catheter 366 and balloons 362, 364 are withdrawn from the patient. A second double flange extension 300 may then be deployed into the right renal artery 24 (FIG. 2).

Figure 47:
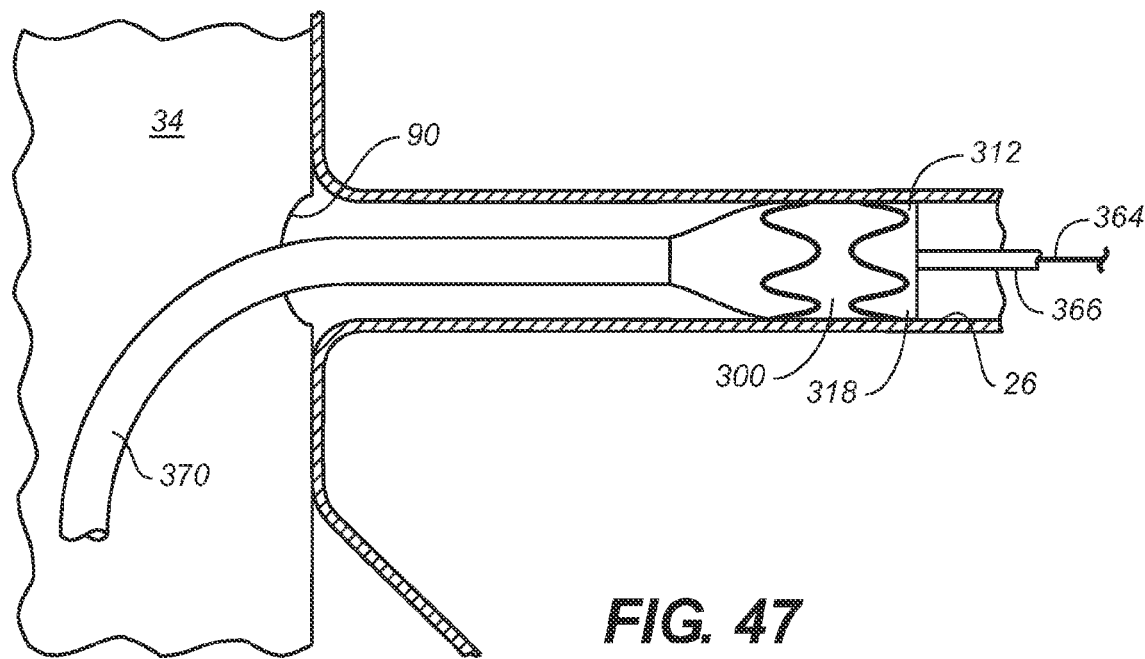
FIG. 47 is a partial schematic view of the portion of the exclusion device and adjacent aorta of FIG. 15, showing an alternative, self expanding, renal extension construction as compared to that of FIG. 38 partially expanded into a final placement position.
Figure 48:
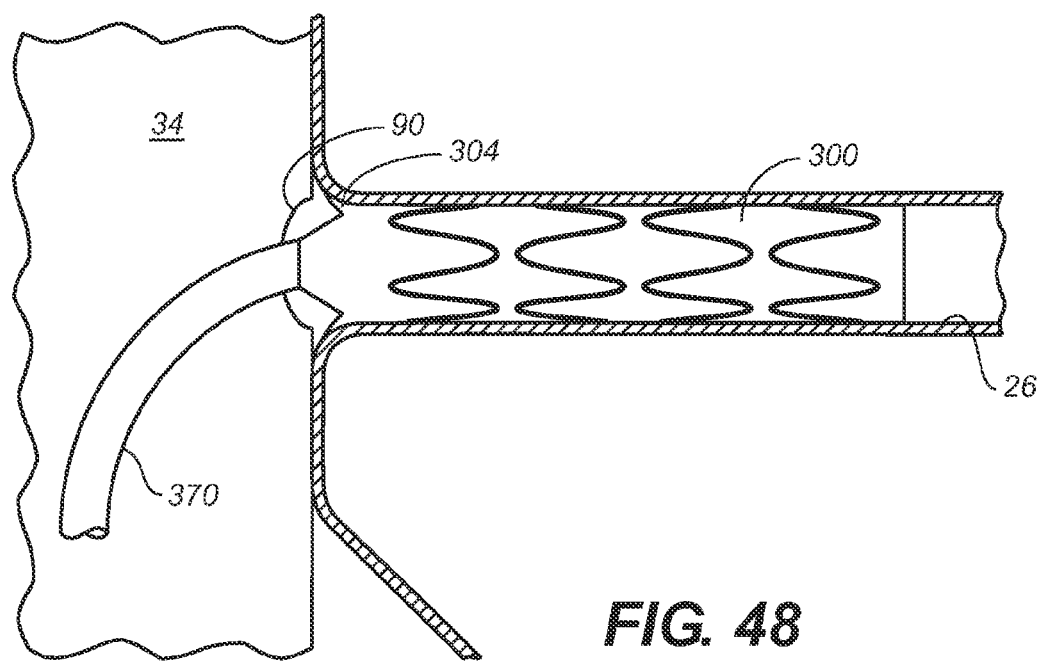
FIG. 48 is a partial schematic view of the portion of the exclusion device and adjacent aorta of FIG. 15, showing the alternative, self expanding, renal extension construction of FIG. 47 further expanded such that the delivery sheath has been retracted where one of the two flanges thereon is expanded.
Figure 49:
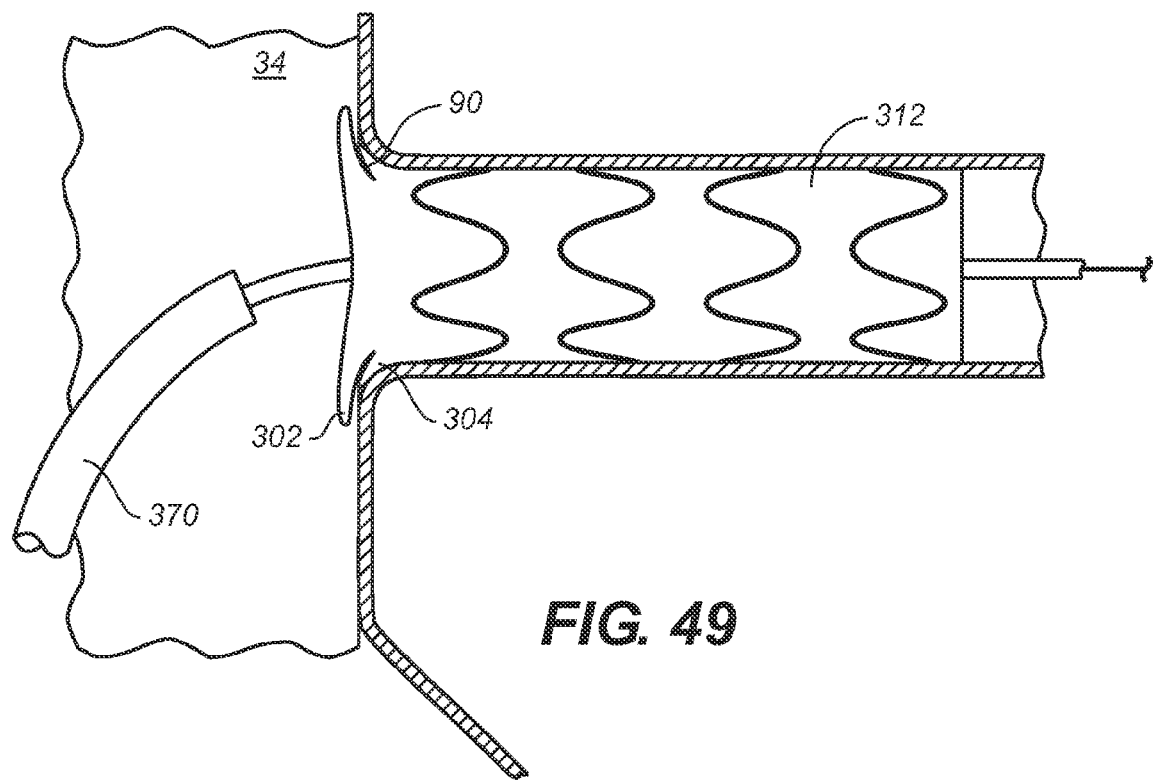
FIG. 49 is a partial schematic view of the portion of the exclusion device and adjacent aorta of FIG. 15, showing the alternative, self expanding, renal extension construction of FIG. 47 fully expanded and deployed in its final placement position.

To deploy the self expanding double flange extension 300, a similar deployment regime to that shown and described in FIGS. 41 to 45 is followed, but balloons 362 and 364 need not be deployed. In this embodiment, as the sheath delivering the extension 300 is retracted, the stent framework 312 and the baskets 322, 324 are self expanding. Thus, as shown in FIG. 47, as the sheath 370 is retracted while the double wall extension 300 therein remain stationary, the stent framework 312 expands, to push the extension body into engagement with the inner wall of the renal artery 26 inwardly of the distal end 318 thereof. The sheath 370 then is further retracted to the position shown in FIG. 48, such that second flange 304 is freed from the sheath 370 and is substantially expanded, but the first flange remains within the sheath. Thence, the sheath 370 is fully retracted to the position in FIG. 49, such that the first flange 302 now bears against, and pushes the body 34 about the aperture 90 in the direction of second flange 304, to pinch the material of the body between the two flanges 302, 304. Then, the sheath 370 and wire 364 and catheter 366 are withdrawn, and a second double flange extension 300 may deployed into the second of the apertures 90 in body 34.

Figure 50:
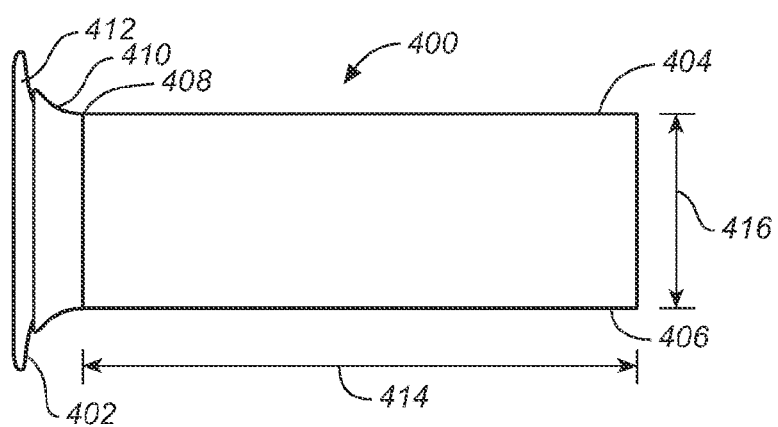
FIG. 50 is a plan view of a braided configuration of a renal extension deployable into the portion of the exclusion device of FIG. 15.

Referring now to FIG. 50, yet another construct of the extension is shown. In this construction, the graft and stent framework structure is modified, such that a braided structure constructed of one or several intermingled graft materials, such as Dacron, and a stent material, such as a shape memory material such as Nitinol, are braided to form a tubular structure. To create the braided tubular structure 404, strands of Dacron or another biocompatible fabric or polymer, is braided with a shape memory material such as Nitinol wire having a diameter of less than one mm, are braided in a ratio of one to 5 strands of Dacron to one strand of wire, to form a braided tube. This tube is cut to length, and the opposed ends are fused or otherwise secured against fraying (or not), and a double flange 402 arrangement, which may have the same general construct as the first and second flanges 302, 304 of the double flange extension 300, is secured to the tube such as by over molding the flanges in an insert mold.

Figure 51:
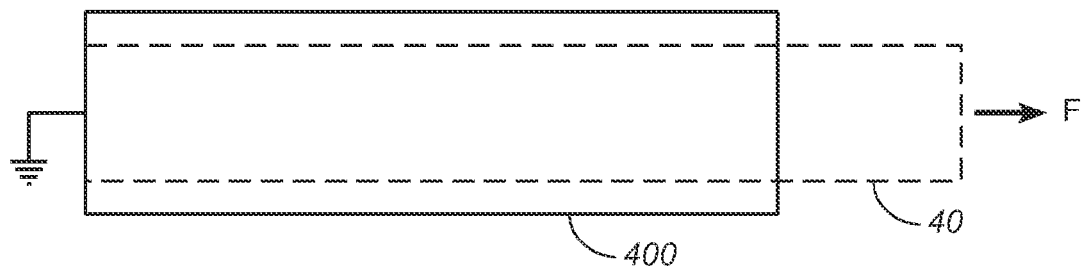
FIG. 51 is a plan view showing the foreshortening elastic self expanding characteristics of the renal extension of FIG. 50.

The braided tubular structure 404 has a free state as shown in FIG. 50, but also stretches in a length direction as shown in FIG. 51, which simultaneously reduces the free diameter of the braided tubular structure 404 (foreshortening), which feature may be used during deployment to ensure loading of a flange of the double flange arrangement 402 with the body 34 of the stent graft about aperture 90. Thus, if the ends of the braided member are stretched apart, as shown by the dashed lines in FIG. 51, the diameter of the tube is decreased. However, the free state of the tube is as shown in solid line outline, and to maintain the extended dashed line outline, a force F must be maintained relative to the opposed ends of the tube. If the force is released, the tube returns to its free, solid line, profile. Thus, where the distal end 406 which is to be deployed within a renal artery, and the proximal end 408 over which first flange 412 and second flange 410 may be molded or otherwise affixed, are pulled apart from their free state, the braided structure 404 becomes internally loaded with a bias which, if unrestrained, tends to urge the opposed ends 408, 406 toward each other until the free state diameter 416 and length 414 are re-attained. This feature may be used to advantage during deployment of the braided extension 400. Specifically, by providing a free state diameter 416 of the braided portion 404 larger than the intended deployment location, i.e., renal artery, diameter, the self expanding tubular portion can be anchored against the renal artery 26 wall, and then stretched as the remainder of the braided extension 400 is deployed, such that upon full deployment of the braided extension, the flanges 410, 412 will be deployed to the exterior and interior of the body 34, and the flange 412 will bear against the inner wall of the body about the aperture 90, and be biased in that direction by the internal loading of the braided tubular portion 404.

Figure 52:
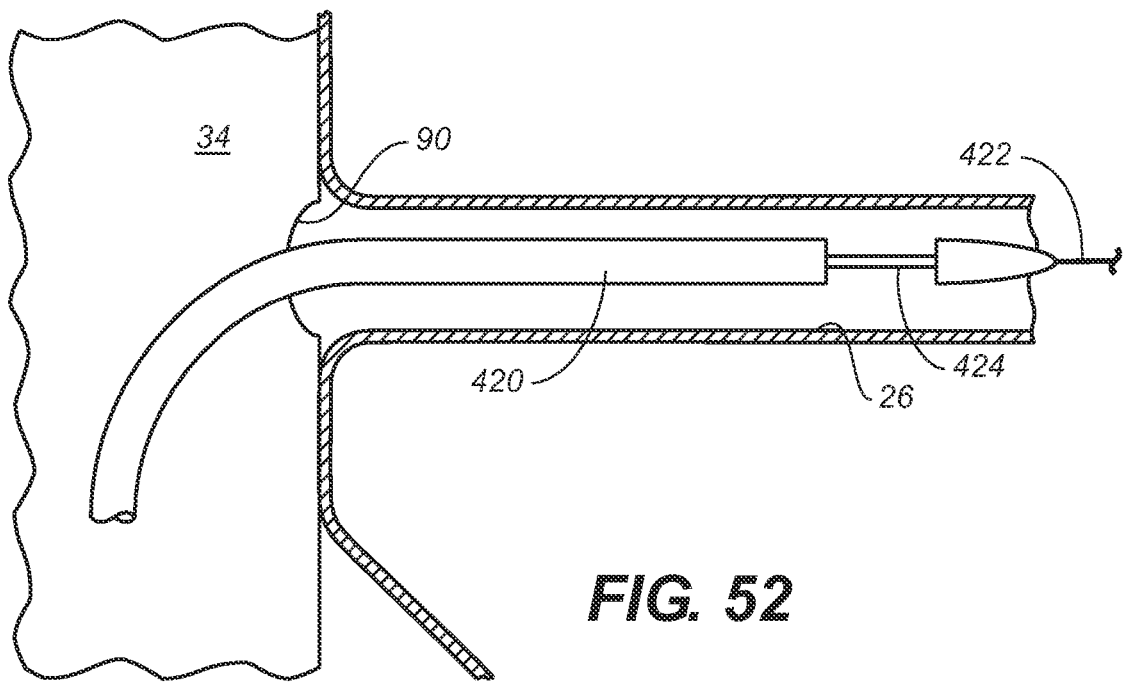
FIG. 52 is a partial schematic view of the portion of the exclusion device and adjacent aorta of FIG. 15, showing a delivery device in position to deploy the alternative, self expanding, renal extension construction of FIG. 50.
Figure 53:
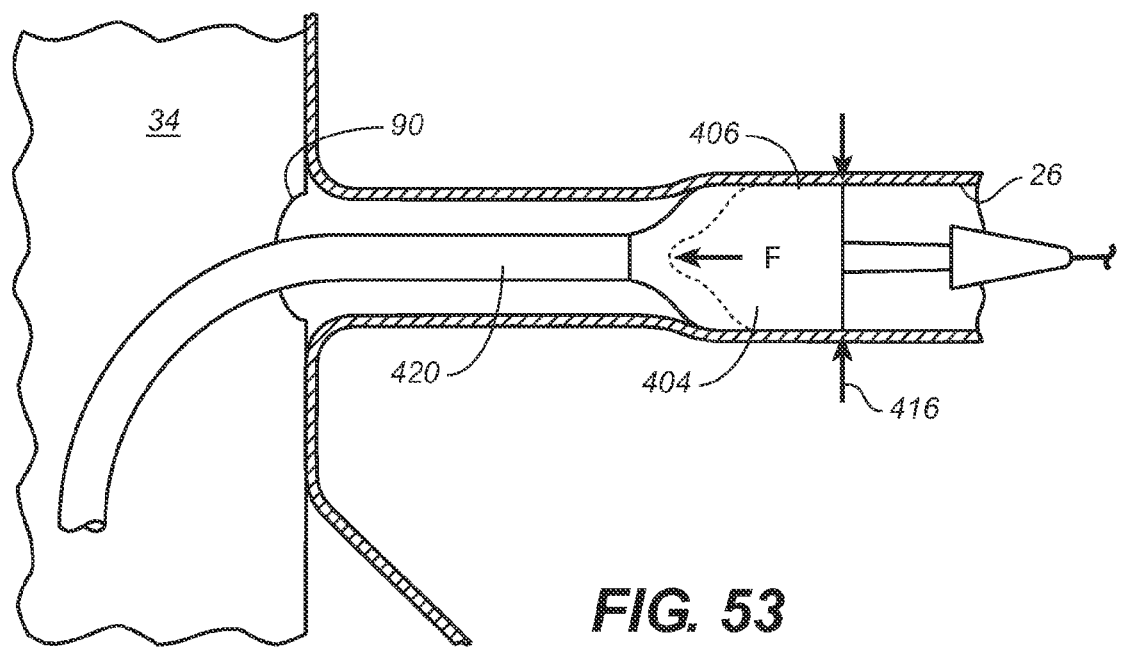
FIG. 53 is a partial schematic view of the portion of the exclusion device and adjacent aorta of FIG. 15, showing the alternative, self expanding, renal extension construction of FIG. 50 partially deployed and in contact with the renal artery adjacent to the distal end of the renal extension.
Figure 54:
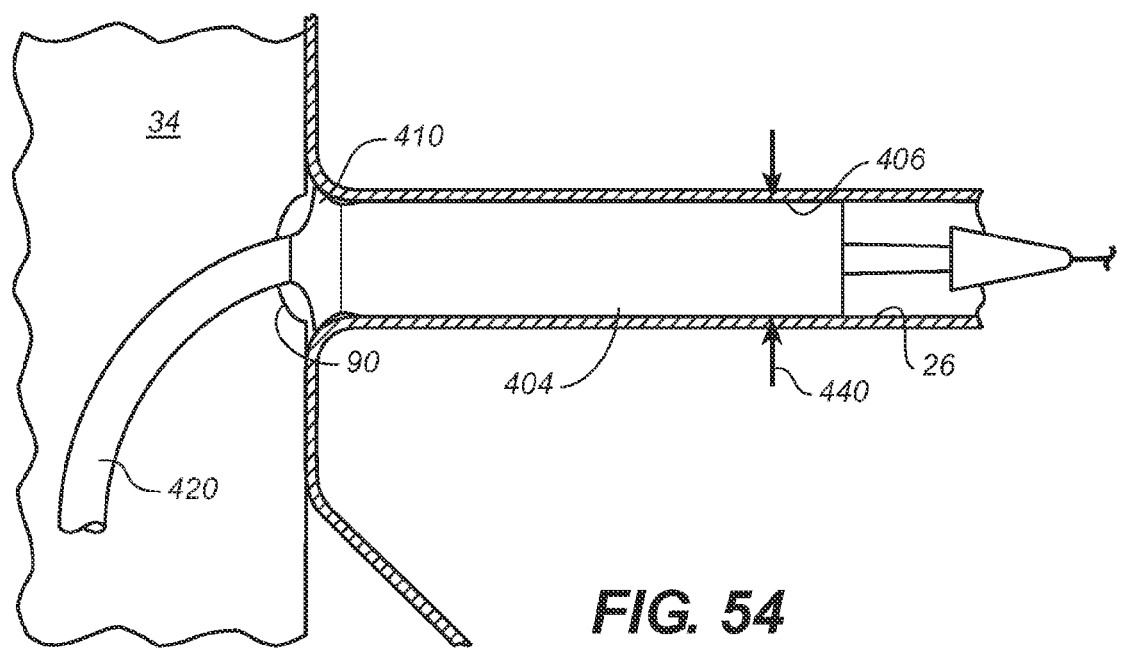
FIG. 54 is a partial schematic view of the portion of the exclusion device and adjacent aorta of FIG. 15, showing the alternative, self expanding, renal extension construction of FIG. 50 nearly fully deployed in a renal artery and adjoining portion of the excluding device.
Figure 55:
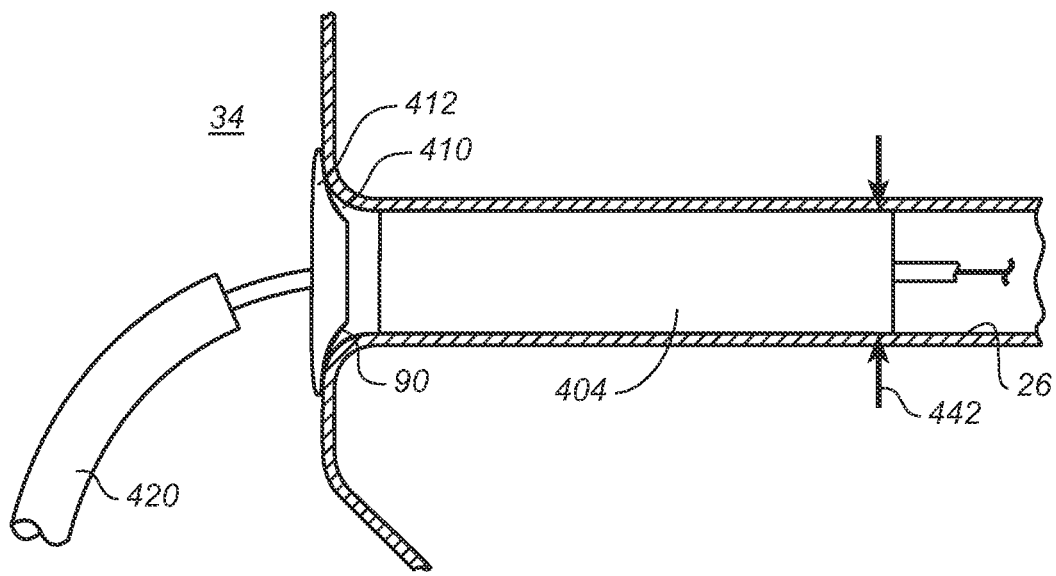
FIG. 55 is a partial schematic view of the portion of the exclusion device and adjacent aorta of FIG. 15, showing the alternative, self expanding, renal extension construction of FIG. 50 in its fully deployed position.

Referring now to FIG. 52, the deployment of the braided extension 400 into a renal artery 26 and stent graft body 34 are shown. Again, body 34 was previously deployed as shown and described with respect to FIGS. 7 to 19 hereof. Again, a delivery sheath 420, into which the braided extension 400 has been previously placed, is directed to the renal artery 26 after being guided along a guide wire 422 which was previously guided through the interior of body 34 and through aperture 90 and thence into the renal artery 26. Once the sheath 420 is so positioned, the location of the distal end 406 of the braided extension and the proximal end of the braided extension are fluoroscopically visualized, to position the distal end 406 a distance from the aperture 90 and body 34 at the aperture greater than the free state length 414 of the braided tubular portion 404. In this position, the sheath 420 is retracted to the position shown in FIG. 53, wherein the distal end 406 of the braided portion 404 is engaged against the renal artery 26 wall. As the tubular braided portion 404 is freed from the sheath 420, it attains its free state diameter 416, which is larger than the free state diameter of the renal artery 26, such that a slight loading of the braided tubular portion 404 against the renal artery wall 26 occurs (which is shown exaggerated in the Figure). This loading assures that the braided tubular portion 404 will remain in contact with the renal artery 26 wall adjacent to the distal end 406 thereon, even if a loading or force in the direction of arrow F is applied to the braided tubular portion 404 that is not yet deployed. Then, as the braided tubular portion 404 is continued to be deployed, by retracting the sheath 420, a force in the direction F is applied to the braided tubular portion 404, such as by slightly retracting an internal stop (not shown) as the sheath 420 is retracted, such that the diameter 440 of the braided tubular member 404 is smaller than the free state diameter 416, but still large enough to maintain the braided tubular portion 404 against the renal artery 26 wall, adjacent distal end 406. In this position, the second flange 410 is released from the sheath 420, and is disposed outwardly of body 34 at the aperture 90, as shown in FIG. 54. Then, the sheath 420 is further retracted, such that the first flange 412 is released inwardly of the aperture 90, which simultaneously releases the braided extension 400 from the sheath 420. When the braided extension 400 becomes free of the sheath 420, the force of the sheath 420 stretching the braided tubular portion 404 in the linear direction is released, which causes the braided tubular portion 404 to retract linearly, thereby causing the flange 412 to push against the inner portion of the body 34 about the flange 90, and causing the body to be loaded in the direction of the renal artery 26, while simultaneously allowing the braided tubular portion 404 to expand diametrically, such that the diameter 442 approaches the free state diameter 416. The sheath 420 guidewire and catheter are then retracted from the patient, and a second braided extension 400 deployed in the second aperture 90 in the body.

Figure 56:
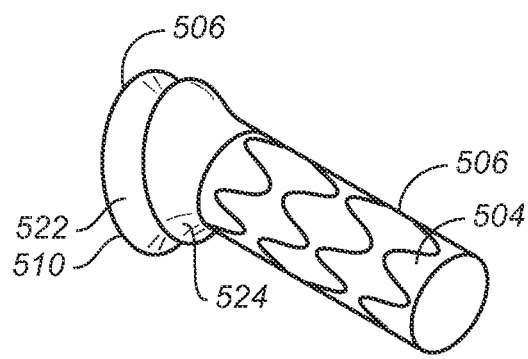
FIG. 56 is a perspective view of an additional configuration of a renal extension, wherein the renal extension is configured to match a specific geometry of the anatomy at the intersection of a renal artery and an aorta.
Figure 57:
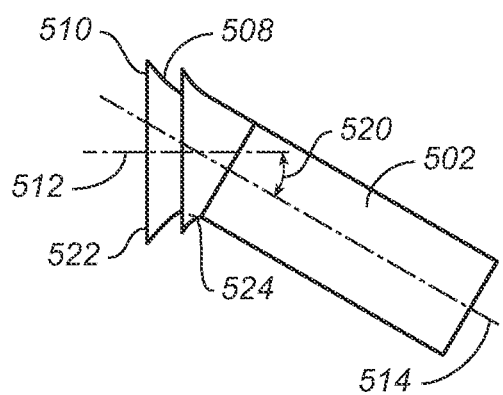
FIG. 57 is a side plan view of the renal extension of FIG. 56.

Referring now to FIGS. 56 and 57, an additional construction of an extension, in this case, a directional extension 500 is shown and described. Directional extension 500 generally includes a tubular extending portion 502, constructed from a graft material 504 and stent framework 506, and a double flange mounting portion 508, such that the base end 510 of the double flange mount portion 506 is disposed generally perpendicular to a first axis 512, and the tubular extension portion 502 extends about axis 514, and the axis 512 and 512 intersect an angle 520. Thus, where the renal artery 26 does not intersect the aorta 10 in a generally perpendicular relation thereto, but is instead offset by a non perpendicular angle, the provision of the tubular portion 502 offset at an angle 520 from a generally longitudinal first axis 512 enables the tubular portion 502 to align with a renal artery of such geometry, while still allowing the flange portion of the extension to engage the body 34 at the aperture 90 generally in the plane of the body wall at the aperture 90.

As with the previous double flange style of construction shown and described with respect to FIGS. 38 to 40 hereof, the flanges include a major diameter flange 522 and a minor diameter flange 524, such that the largest diameter of each flange is larger than an aperture 90 in a stent graft body 34 into which the directional extension 500 will be deployed, and the major diameter flange 522 is deployed within, and will bear against, the interior of body 34 at the aperture 90, and the minor diameter flange 524 will be deployed outside of, and bear against, the body about the aperture 90. Likewise, baskets similar to those of FIG. 40 may be used to support the flanges 522, 524, such that the surfaces of the flange are formed by molding a thin polymer, such as silicone, over the baskets. In this embodiment, the baskets are also configured to provide the angular deviation of the extension 500, and are again preferably configured of a shape memory material.

Figure 58:
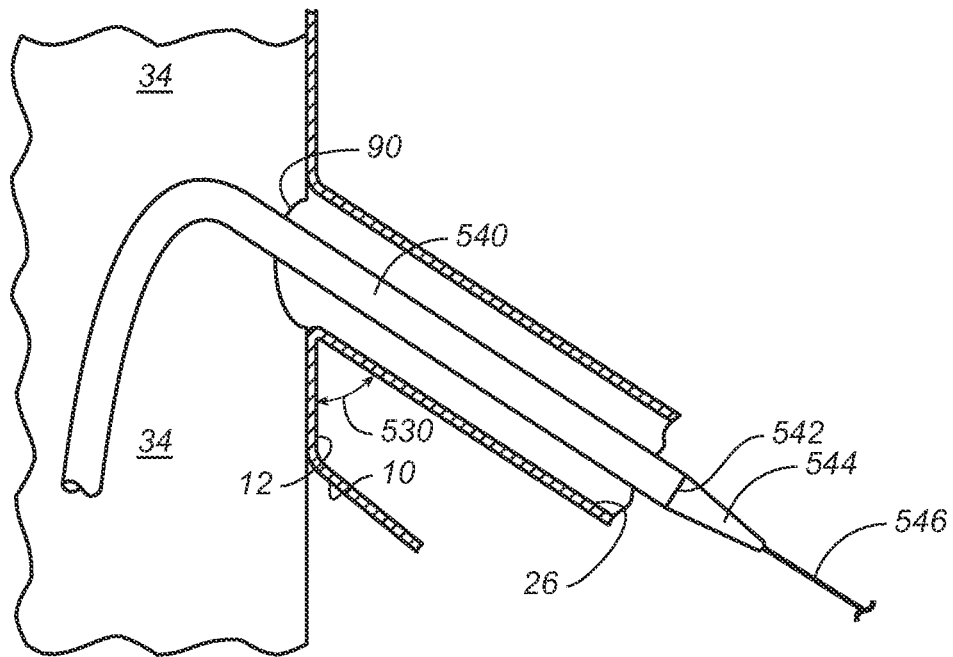
FIG. 58 is a partial sectional view of a specific anatomy of a renal artery branching from an aorta, having the portion of exclusion device of FIG. 15 positioned in the aorta, and a delivery device positioned to deploy the renal extension of FIG. 56.
Figure 59:
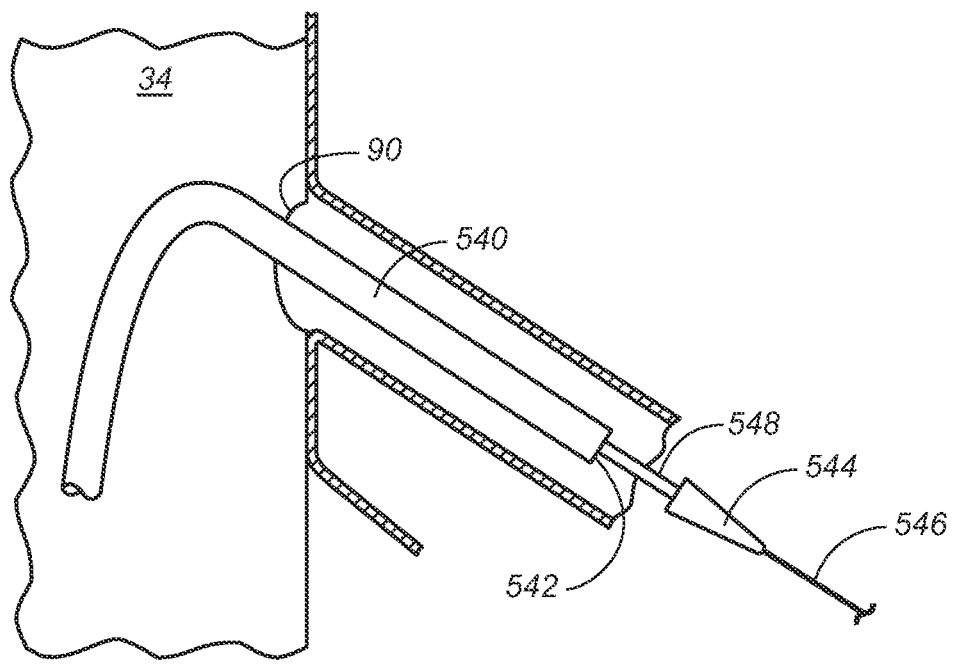
FIG. 59 is a partial sectional view of a specific anatomy of a renal artery branching from an aorta, having the portion of exclusion device of FIG. 15 positioned in the aorta, and a delivery device positioned in a ready to deploy condition to deploy the renal extension of FIG. 56.
Figure 60:
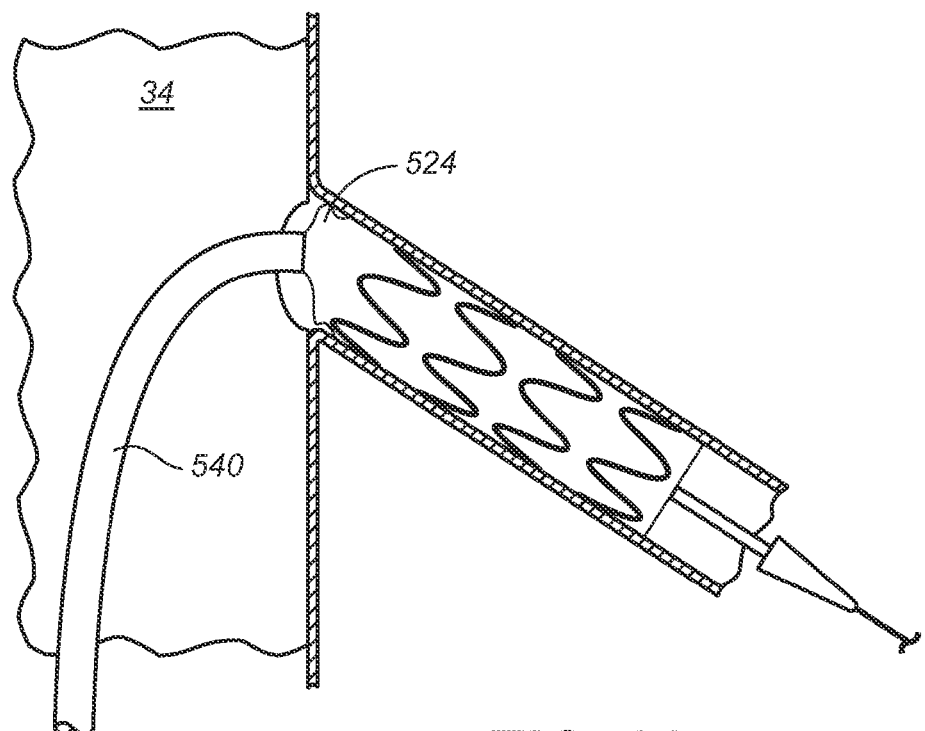
FIG. 60 is a partial sectional view of a specific anatomy of a renal artery branching from an aorta, having the portion of exclusion device of FIG. 15 positioned in the aorta, and the renal extension of FIG. 56 partially deployed.
Figure 61:
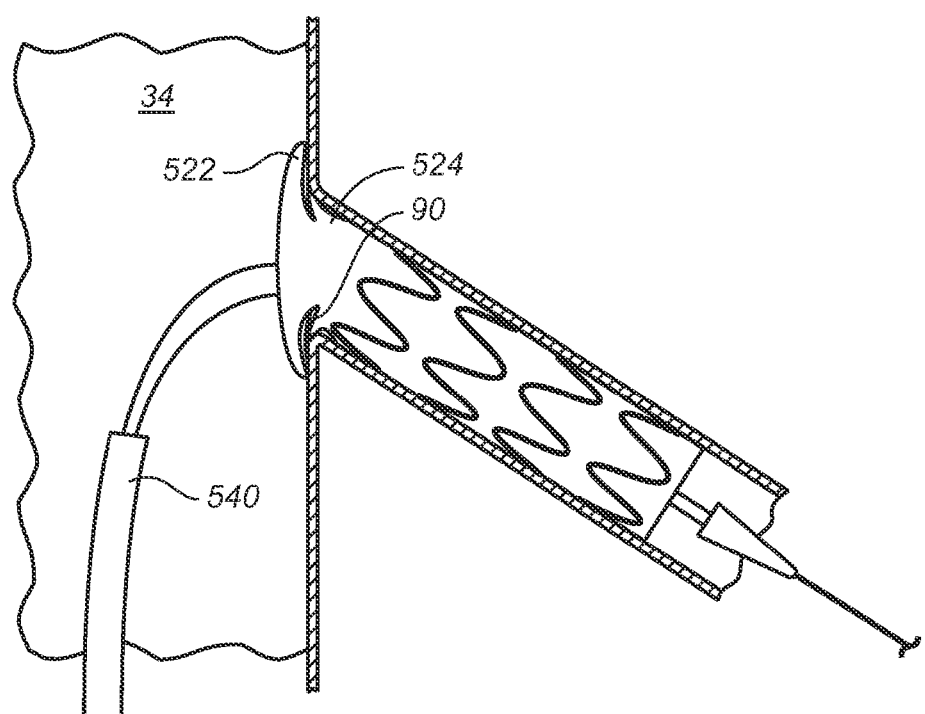
FIG. 61 is a partial sectional view of a specific anatomy of a renal artery branching from an aorta, having the portion of exclusion device of FIG. 15 positioned in the aorta, and the renal extension of FIG. 56 fully deployed and extending from the exclusion device and into sealing engagement with the wall of the renal artery.

Referring now to FIGS. 59 to 61, the deployment of the directional extension 500 within the stent graft body 34 previously deployed as shown and described with respect to FIGS. 7 to 19 hereof. As shown in FIG. 58, body 34 is deployed within aorta 10, where renal artery 26 extends from the aorta 10 at an acute angle 530 with respect to the aorta wall 12, rather than generally perpendicular thereto as shown and described with respect to FIGS. 7 to 19 hereof. Once the body 34 is deployed as previously described, a sheath 540, having the directional extension 500 held in a compressed state therein, is directed through body 34 and aperture 90 and terminates within the renal artery 26 at a position beyond the deployment location of the directional extension 500. The directional extension is held within the sheath 540, adjacent the sheath end 542, by compressing the extension 500 and locating it within the open end of the sheath, with the guidewire 546 and a tapered catheter 548 (FIG. 59) extending therethrough, as shown and described with respect to the previous constructions of the extension discussed herein.

Once the sheath is positioned as shown in FIG. 57, the tapered tip 544 is pushed off the sheath end 542 by pushing on the tapered catheter 548, which exposes the compressed directional extension within the sheath 540 which expands by expansion of the shape memory material, to engage against the inner wall of renal artery 26 as shown in FIG. 59 where the minor diameter flange 524 is shown partially expanded, and located adjacent to and exterior of the aperture 90. As the sheath 540 is continued in a retraction direction, the major diameter flange 522 is released therefrom, immediately adjacent to and interior of the aperture 90, pinching the body 34 about the aperture 90 between the flanges 522, 524 to seal the aperture. Although the directional extension 500 is shown and described as a self expanding stent, other configurations, such as a non-self expanding stent having a graft material and a wire framework which must be expanded by balloons, is also contemplated.

To use a directional extension, the local aorta and artery geometry and size is first visualized fluoroscopically, and a directional stent having an angle 520 corresponding to the deviation from perpendicular of the intersection of the renal artery 26 with the aorta is selected. The directional extension 500 is also selected to have an outer circumference at least as large, as and preferably slightly larger than, the diameter of the renal artery 26, to ensure sealing of the tubular portion thereof in the artery. Likewise, by virtue of the double flange construction, the directional extension may be deployed in a manner that the inner, i.e., minor diameter flange 524, is biased against the interior of the body 34 about the aperture 90.

Figure 62:
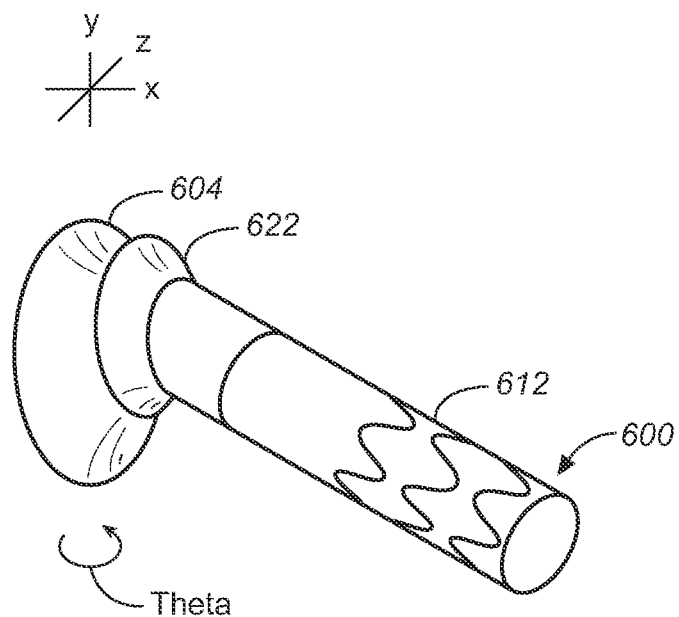
FIG. 62 is a perspective view of an additional configuration of a renal extension, wherein the renal extension is configured to match a specific geometry of the anatomy at the intersection of a renal artery and an aorta, and having the capability to modify the relative position as between the flange and tubular extension portions thereof.
Figure 63:
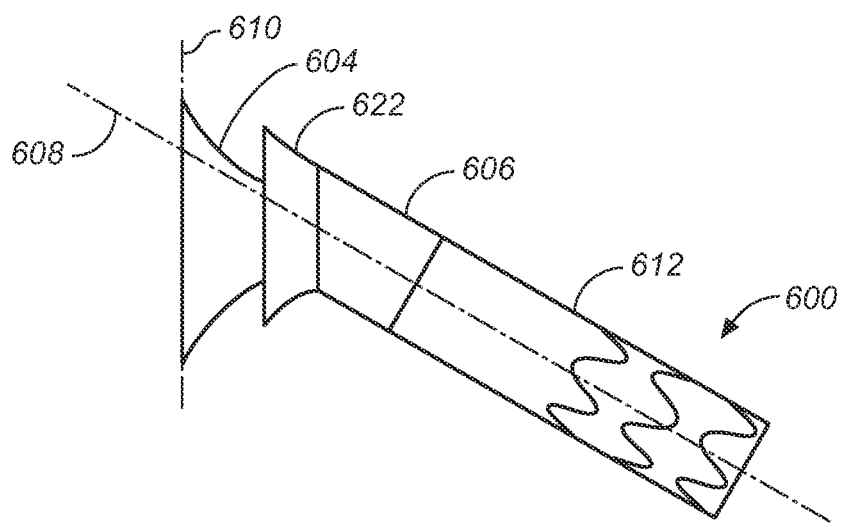
FIG. 63 is a side plan view of the renal extension of FIG. 64.

An additional construction of a directional extension is shown in FIGS. 62 and 63. In this construction, an in situ configurable extension 600 includes a tubular portion 602 configured of a stent frame and exclusion material for extension into the renal artery 24, 26 and a double flange portion 604, but in contrast to the directional extension 500, the in situ configurable extension 600 includes an extended polymer portion 606, which is configured as a thin polymer sheet, which may be molded in place, extending from the minor diameter flange 622 of the double flange construct to the stent frame and exclusion material portion 612 of the extension 600, such that the angle of the centerline 608 of the tubular portion 602 and the base plane 610 of the double flange arrangement may be varied during deployment, to enable the extension 600 to be angularly configured during deployment. This is accomplished by first positioning the tubular portion 602 in the renal artery, and then aligning the delivery device, such as a sheath, within the general center of the aperture into which the extension 600 is deployed, to provide additional deviation between the base plane 610 and centerline 608. It is specifically contemplated that more than one thin walled sheet regions, enabling multiple turns in the extension, may be provided, including within the stent frame and exclusion material portion 612. Thus, several degrees of freedom of the position of the double flange portion 606 with respect to the stent frame and exclusion material portion 612 are provided, such that the double flange portion can move in the x,y,z and theta directions with respect to the main body 34.

Although several constructions of flanges and tubular portions of a extension for spanning between a stent graft body and an adjacent opening of a branch artery or vessel have been shown and described, each construct of the tubular portion, may be employed with each shown and described flange construct. Additionally, each construct may be deployed such that loading occurs naturally as the tubular portion, in conjunction with its anchoring or seating in the artery, may be positioned in the branch artery such that a bias in the direction of the artery may be ensured to ensure that the flange held within the body bears against the interior of the stent graft body about the aperture through which the extension extends. Thus, sealing of the extension with respect to the aperture in the stent graft may be ensured. Also, although the extensions are shown and described as renal extensions in a thoracic region of a patient, they may also be employed with a main body of a stent graft configured for aortic arch, or other, aneurysmal, sites.

What is claimed is:

1. An exclusion device for excluding fluid contact to an abnormality in a body flow lumen, comprising:
   a body portion having a wall portion and at least opposed first and second open ends;
   an aperture extending through said wall portion, said aperture alignable with an opening of a branch feature into the body flow lumen; and
   an extension receivable within said aperture and extendible there from into the branch feature extending from the body flow lumen, said extension including:
      a generally tubular body having a first end and a second end, the generally tubular body including an excluding material and at least one stent; and
      a flange having a generally frustoconical internal support feature separate from the at least one stent of the generally tubular body, the generally frustoconical internal support feature encapsulated within a biocompatible polymer or held by one of the following overmolded materials: silicone polyurethane, polyurethane blends, polyurethane alloys, ePTFE, PET, polypropylene, polyethylene or other biocompatible materials, the biocompatible polymer or overmolded material defining a generally tapered outer circumferential surface of the flange, the flange located adjacent to and coupled to said first end of said generally tubular body and adapted to sealingly engage with said body portion adjacent said aperture, the generally tapered outer circumferential surface tapering from a first end having a first diameter to a second end having a second diameter, wherein the first diameter is larger than the second diameter;
   wherein said extension is configured to urge said flange of said extension and said body portion in contact adjacent to said aperture such that the generally tapered outer circumferential surface of said flange is adapted to engage against said aperture, the first end of the generally tapered outer circumferential surface is configure to be disposed within said body portion, and the second end of the generally tapered outer circumferential surface is configured to be disposed outside of the body portion.

2. An exclusion device for excluding fluid contact to an abnormality in a body flow lumen, comprising:
   a body portion having a wall portion and at least opposed first and second open ends;
   an aperture extending through said wall portion, said aperture alignable with an opening of a branch feature into the body flow lumen; and
   an extension receivable within said aperture and extendible there from into the branch feature extending from the body flow lumen;
   said extension including:
      a generally tubular body having a first end and a second end, the generally tubular body including an excluding material and at least one stent; and
      a flange having a generally frustoconical internal support feature separate from the at least one stent of the generally tubular body, the generally frustoconical internal support feature encapsulated within a biocompatible polymer or held by one of the following overmolded materials: silicone polyurethane, polyurethane blends, polyurethane alloys, ePTFE, PET, polypropylene, polyethylene or other biocompatible materials, the biocompatible polymer or overmolded material defining a generally tapered outer circumferential surface of the flange, the flange adapted to be located adjacent to and coupled to said first end of said generally tubular body to sealingly engage with said body portion adjacent said aperture, the generally tapered outer circumferential surface tapering from a first end having a first diameter to a second end having a second diameter, wherein the first diameter is larger than the second diameter;
   wherein said extension is configured to urge said flange of said extension and said body portion in contact adjacent to said aperture such that the generally tapered outer circumferential surface of said flange is adapted to engage against said aperture, the first end of the generally tapered outer circumferential surface is configured to be disposed within said body portion, and the second end of the generally tapered outer circumferential surface is configured to be disposed outside of the body portion.

3. The exclusion device of claim 2, wherein said generally frustoconical internal support feature is formed of a retained biased structure.

4. The exclusion device of claim 3, wherein said retained biased structure is a wire mesh.

5. The exclusion device of claim 3, wherein said retained biased structure includes at least one wire basket.

6. An exclusion device for excluding fluid contact to an abnormality in a body flow lumen, comprising:
   a body portion having a wall portion and at least opposed first and second open ends;
   an aperture extending through said wall portion, said aperture alignable with an opening of a branch feature into the body flow lumen; and
   an extension receivable within said aperture and extendible there from into the branch feature extending from the body flow lumen, said extension including:
      a generally tubular body having a first end and a second end, the generally tubular body including an excluding material and at least one stent; and
      a flange including a first flange portion and a second flange portion, a generally frustoconical internal support feature encapsulated within a biocompatible material and disposed within one of the first and second flange portions, the generally frustoconical internal support structure being separate from the at least one stent of the generally tubular body, wherein the first end of the generally tubular body is received within the flange, wherein said first flange portion is configured to be retained within said body portion, and said second flange portion is configured to be positioned exterior to said body portion.

7. The exclusion device of claim 6, wherein said frustoconical support feature includes a first frustoconical support feature disposed within said first flange portion and a second frustoconical support feature disposed within said second flange portion.

8. An exclusion device for excluding fluid contact to an abnormality in a body flow lumen, comprising:
   a body portion having a wall portion and at least opposed first and second open ends;
   an aperture extending through said wall portion, said aperture alignable with an opening of a branch feature into the body flow lumen; and
   an extension receivable within said aperture and extendible there from into the branch feature extending from the body flow lumen, said extension including:
   a generally tubular body having a first end and a second end, the generally tubular body including an excluding material and at least one stent;
   a flange having a first flange portion retained within said body portion and a second flange portion positioned exterior to said body portion; and
   a polymer sheet portion disposed between the second flange portion and the first end of the generally tubular body, wherein said first flange portion is positioned about a first flange axis and the generally tubular body includes a longitudinal axis centerline which is angularly offset from the first flange axis when said extension is in a deployed configuration with said first flange portion within said body portion, said second flange portion exterior to said body portion, and said generally tubular body disposed within the branch feature and in a radially expanded configuration.

* * * * *

UNITED STATES PATENT AND TRADEMARK OFFICE
CERTIFICATE OF CORRECTION

PATENT NO.        : 8,715,336 B2
APPLICATION NO.   : 11/737432
DATED             : May 6, 2014
INVENTOR(S)       : Chu et al.

Page 1 of 1

It is certified that error appears in the above-identified patent and that said Letters Patent is hereby corrected as shown below:

In the Claims

In column 22, line 24 "generally tubular body to" should read -- "generally tubular body and adapted to" --

Signed and Sealed this
Fourteenth Day of July, 2015

Michelle K. Lee
*Director of the United States Patent and Trademark Office*